US009412476B2

(12) United States Patent
Eckhoff et al.

(10) Patent No.: US 9,412,476 B2
(45) Date of Patent: *Aug. 9, 2016

(54) SYSTEMS, DEVICES, METHODS, AND COMPOSITIONS INCLUDING FLUIDIZED X-RAY SHIELDING COMPOSITIONS

(75) Inventors: Philip A. Eckhoff, Bellevue, WA (US); William H. Gates, III, Redmond, WA (US); Peter L. Hagelstein, Carlisle, MA (US); Roderick A. Hyde, Redmond, WA (US); Jordin T. Kare, Seattle, WA (US); Robert Langer, Newton, MA (US); Erez Lieberman, Cambridge, MA (US); Eric C. Leuthardt, St. Louis, MO (US); Nathan P. Myhrvold, Bellevue, WA (US); Michael Schnall-Levin, Cambridge, MA (US); Clarence T. Tegreene, Bellevue, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 1171 days.

This patent is subject to a terminal disclaimer.

(21) Appl. No.: 13/373,139

(22) Filed: Nov. 3, 2011

(65) Prior Publication Data

US 2013/0112924 A1    May 9, 2013

(51) Int. Cl.
  *G21F 1/00*  (2006.01)
  *G21F 1/06*  (2006.01)
  *G21F 1/08*  (2006.01)
  *G21F 1/10*  (2006.01)
  *G21F 1/02*  (2006.01)
  *G21F 3/00*  (2006.01)
  *A61B 6/10*  (2006.01)
  *G21F 3/02*  (2006.01)

(52) U.S. Cl.
  CPC ... *G21F 1/02* (2013.01); *A61B 6/10* (2013.01); *G21F 3/00* (2013.01); *G21F 3/02* (2013.01)

(58) Field of Classification Search
  None
  See application file for complete search history.

(56) References Cited

U.S. PATENT DOCUMENTS

| | | | |
|---|---|---|---|
| 2,747,105 A * | 5/1956 | Fitzgerald et al. | 250/515.1 |
| 3,514,607 A * | 5/1970 | Webster | 250/519.1 |
| 3,818,229 A * | 6/1974 | Long, Jr. | 252/478 |
| 4,195,229 A | 3/1980 | Suzuki | |
| 4,957,943 A | 9/1990 | McAllister et al. | |
| 5,130,342 A | 7/1992 | McAllister et al. | |
| 5,245,195 A | 9/1993 | Shah et al. | |
| 5,745,925 A | 5/1998 | Ghilardi et al. | |
| 5,960,794 A | 10/1999 | Shaw | |
| 6,198,806 B1 | 3/2001 | Prins | |
| 7,142,634 B2 | 11/2006 | Engler et al. | |
| 7,193,230 B2 | 3/2007 | Lagace et al. | |
| 7,197,108 B2 | 3/2007 | Watanabe et al. | |
| 7,608,847 B2 | 10/2009 | Rees | |
| 7,973,299 B2 | 7/2011 | Rees | |
| 8,158,432 B2 | 4/2012 | Grof et al. | |
| 8,354,658 B1 | 1/2013 | Smith et al. | |
| 2005/0211930 A1* | 9/2005 | DeMeo et al. | 250/516.1 |
| 2007/0138415 A1 | 6/2007 | Rees | |
| 2009/0050812 A1 | 2/2009 | Dunleavy et al. | |
| 2009/0184269 A1 | 7/2009 | Rees | |

FOREIGN PATENT DOCUMENTS

| | | | | |
|---|---|---|---|---|
| DE | 3224105 A1 * | 1/1984 | | G21F 1/026 |
| JP | 2008-008102 | 1/2008 | | |
| KR | 2001056190 | * | 7/2001 | |

OTHER PUBLICATIONS

Kerur et al. A novel method for the determination of x-ray mass attenuation coefficients. Appl. Radiat. Isot. vol. 42. No. 6, pp. 571-575, 1991.*
Roy et al. Shielding for neutron scattered dose to the fetus in patients treated with 18 MV x-ray beams. Med. Phys. 27 (8) Aug. 2000.*
Antonio et al.; "Physical Characteristics of Barite Plaster Used for X-Ray Shielding—Part One"; printed on Oct. 24, 2011; 5 pages.

* cited by examiner

*Primary Examiner* — Tanisha Diggs
(74) *Attorney, Agent, or Firm* — Fogg & Powers LLC

(57) ABSTRACT

Systems, devices, methods, and compositions are described for providing an x-ray shielding system including a flexible layer including a support structure having a plurality of interconnected interstitial spaces that provide a circulation network for an x-ray shielding fluid composition.

24 Claims, 6 Drawing Sheets

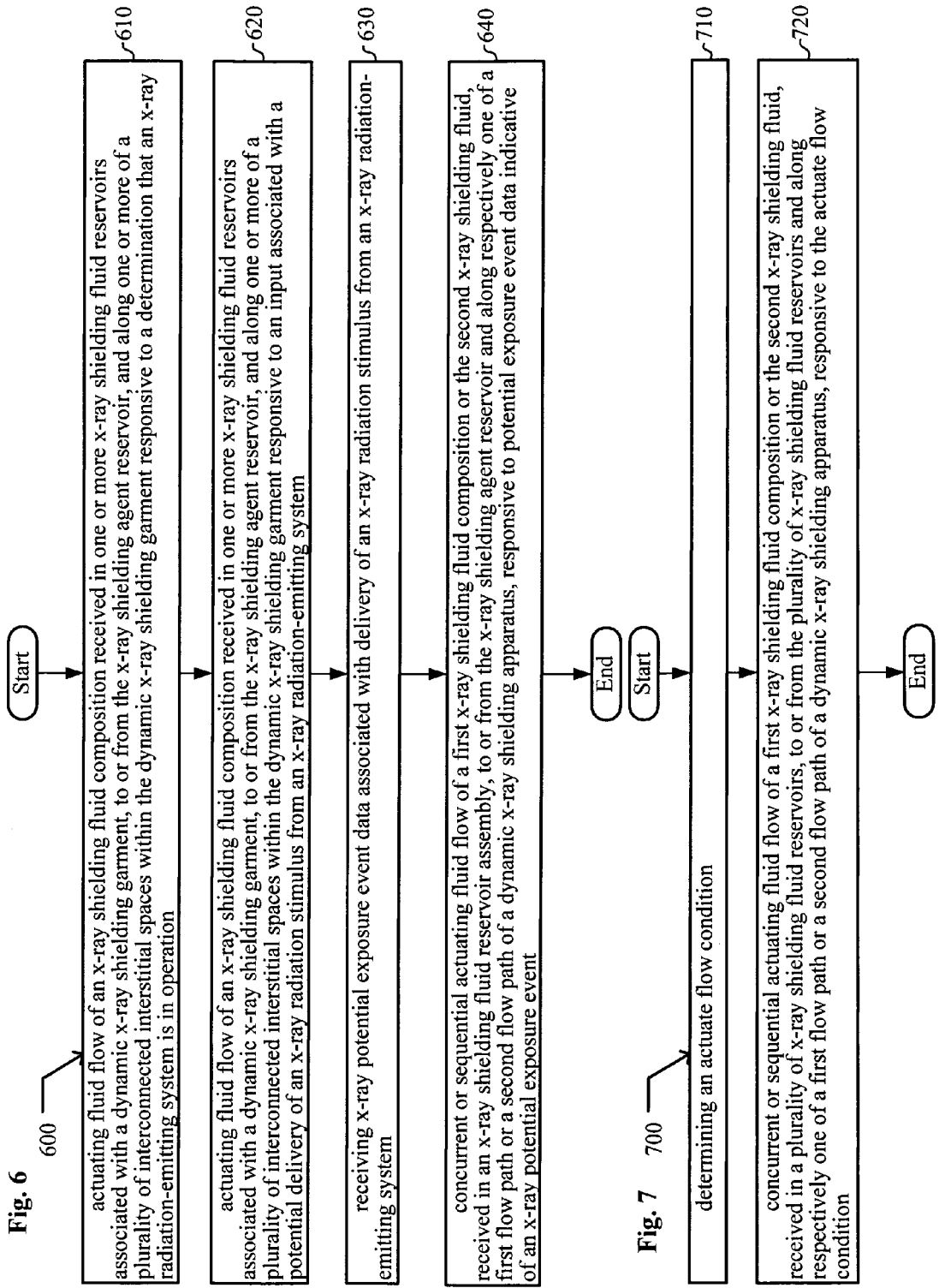

SYSTEMS, DEVICES, METHODS, AND COMPOSITIONS INCLUDING FLUIDIZED X-RAY SHIELDING COMPOSITIONS

SUMMARY

In an aspect, the present disclosure is directed to, among other things, an x-ray shielding fluid composition including a plurality of x-ray shielding particles, each having at least a first x-ray shielding agent and a second x-ray shielding agent, and a carrier fluid. In an embodiment, the second x-ray shielding agent includes one or more absorption edges different from the first x-ray shielding agent. In an embodiment, the plurality of x-ray shielding particles includes a second x-ray having one or more characteristic x-ray absorption edges different from the first x-ray shielding agent. In an embodiment, the second x-ray shielding agent includes one or more k-edges, or one or more l-edges, different from the first x-ray shielding agent. In an embodiment, the plurality of x-ray shielding particles includes a second x-ray having an x-ray mass attenuation coefficient different from the first x-ray shielding agent. In an embodiment, the plurality of x-ray shielding particles include a second x-ray having at least one k-edge having an energy level lower than at least one k-edge of the first x-ray shielding agent In an embodiment, the plurality of x-ray shielding particles include a second x-ray having at least one k-edge or l-edge corresponding to an x-ray energy absorption minimum of the first x-ray shielding agent.

In an aspect, the present disclosure is directed to, among other things, an x-ray shielding fluid composition including at least a first x-ray shielding agent and a second x-ray shielding agent, the second x-ray shielding agent having one or more absorption edges different from the first x-ray shielding agent, and a carrier fluid. In an embodiment, the x-ray shielding fluid composition includes a third x-ray shielding agent having one or more absorption edges different from the second x-ray shielding agent and the first x-ray shielding agent. In an embodiment, the x-ray shielding fluid composition includes a fourth x-ray shielding agent, the fourth x-ray shielding agent having one or more absorption edges different from the third x-ray shielding, the second x-ray shielding agent, and the first x-ray shielding agent. In an embodiment, the x-ray shielding fluid composition includes a fifth x-ray shielding agent, the fifth x-ray shielding agent having one or more absorption edges different from the fourth x-ray shielding agent, the third x-ray shielding, the second x-ray shielding agent, and the first x-ray shielding agent.

In an aspect, the present disclosure is directed to, among other things, dynamic x-ray shielding garments (e.g., aprons, coats, eye protectors, gloves, neck protectors, pants, scrub caps, shirts, skirts, sleeves, socks, surgical scrubs, vests, etc.) including at least a first layer including a support structure having a plurality of interconnected interstitial spaces that provide a circulation network for an x-ray shielding fluid composition. In an embodiment, the support structure is configured to constrain the x-ray shielding fluid composition to move along one or more of the plurality of interconnected interstitial spaces. In an embodiment, a dynamic x-ray shielding garment includes at least one x-ray shielding fluid reservoir assembly including one or more x-ray shielding fluid reservoirs. In an embodiment, the x-ray shielding fluid reservoir assembly is structured and arranged to hold the x-ray shielding fluid composition and to selectively enable fluid communication between one or more x-ray shielding fluid reservoirs and the plurality of interconnected interstitial spaces. In an embodiment, the dynamic x-ray shielding garment includes an x-ray shielding fluid supply controller operable to manage fluid flow of the x-ray shielding fluid composition to or from the x-ray shielding agent reservoir assembly, and along one or more of the plurality of interconnected interstitial spaces.

In an aspect, the present disclosure is directed to, among other things, a dynamic x-ray shielding method including receiving x-ray potential exposure event data associated with delivery of an x-ray radiation stimulus from an x-ray radiation-emitting system. In an embodiment, the dynamic x-ray shielding method includes directing fluid flow of an x-ray shielding fluid composition received in an x-ray shielding fluid reservoir assembly associated with a dynamic x-ray shielding garment, to or from the x-ray shielding agent reservoir, and along one or more of a plurality of interconnected interstitial spaces within the dynamic x-ray shielding garment, responsive to the x-ray potential exposure event data.

In an aspect, the present disclosure is directed to, among other things, an x-ray shielding method including actuating fluid flow of an x-ray shielding fluid composition received in one or more x-ray shielding fluid reservoirs associated with a dynamic x-ray shielding garment, to or from the x-ray shielding agent reservoir, and along one or more of a plurality of interconnected interstitial spaces within the dynamic x-ray shielding garment responsive to a determination that an x-ray radiation-emitting system is in operation.

In an aspect, the present disclosure is directed to, among other things, an x-ray shielding method including actuating fluid flow of an x-ray shielding fluid composition received in one or more x-ray shielding fluid reservoirs associated with a dynamic x-ray shielding garment, to or from the x-ray shielding agent reservoir, and along one or more of a plurality of interconnected interstitial spaces within the dynamic x-ray shielding garment responsive to an input associated with a potential delivery of an x-ray radiation stimulus from an x-ray radiation-emitting system.

In an aspect, the present disclosure is directed to, among other things, a dynamic x-ray shielding system including an x-ray shielding fluid reservoir configured to store and supply at least a first x-ray shielding fluid composition and a second x-ray shielding fluid composition. In an embodiment, the dynamic x-ray shielding system includes at least a first layer including a first flow path in fluid communication with the x-ray shielding fluid reservoir assembly and configured to receive the first x-ray shielding fluid composition. In an embodiment, the first flow path includes a first flow valve assembly selectively actuatable between an open state which permits fluid flow through the first flow valve assembly such that the first x-ray shielding fluid composition flows from the x-ray shielding fluid reservoir assembly along at least a portion of the first flow path, and a restrict state which restricts fluid flow through the first flow valve assembly.

In an embodiment, the dynamic x-ray shielding system includes a second layer including a second flow path in fluid communication with the x-ray shielding fluid reservoir assembly and configured to receive the second x-ray shielding fluid composition. In an embodiment, the second flow path includes a second flow valve assembly selectively actuatable between an open state which permits fluid flow through the second flow valve assembly such that the second x-ray shielding fluid composition flows from the x-ray shielding fluid reservoir assembly along at least a portion of the first flow path, and a restrict state which restricts fluid flow through the second flow valve assembly.

In an embodiment, the dynamic x-ray shielding system includes an x-ray shielding fluid supply controller associated with at least the first flow valve assembly and the second flow valve assembly and configured to selectively actuate the first or the second flow valve assembly to regulate fluid flow of a defined quantity of at least one of the first x-ray shielding fluid composition or the second x-ray shielding fluid composition from the reservoir, through at least one of the first flow valve or the second flow valve, into the at least a portion of the first flow path or the second flow path.

In an aspect, the present disclosure is directed to, among other things, a dynamic x-ray shielding method including receiving x-ray potential exposure event data associated with delivery of an x-ray radiation stimulus from an x-ray radiation-emitting system. In an embodiment, the dynamic x-ray shielding method includes concurrent or sequential actuating fluid flow of a first x-ray shielding fluid composition or the second x-ray shielding fluid, received in an x-ray shielding fluid reservoir assembly, to or from the x-ray shielding agent reservoir and along respectively one of a first flow path or a second flow path of a dynamic x-ray shielding apparatus, responsive to potential exposure event data indicative of an x-ray potential exposure event.

In an aspect, the present disclosure is directed to, among other things, a dynamic x-ray shielding method including determining an actuate flow condition. In an embodiment, the dynamic x-ray shielding method includes concurrent or sequential actuating fluid flow of a first x-ray shielding fluid composition or the second x-ray shielding fluid, received in a plurality of x-ray shielding fluid reservoirs, to or from the plurality of x-ray shielding fluid reservoirs and along respectively one of a first flow path or a second flow path of a dynamic x-ray shielding apparatus, responsive to the actuate flow condition.

BRIEF DESCRIPTION OF THE FIGURES

FIG. 6 shows a flow diagram of a method according to one embodiment.

FIG. 7 shows a flow diagram of a method according to one embodiment.

DETAILED DESCRIPTION

Figure 1:
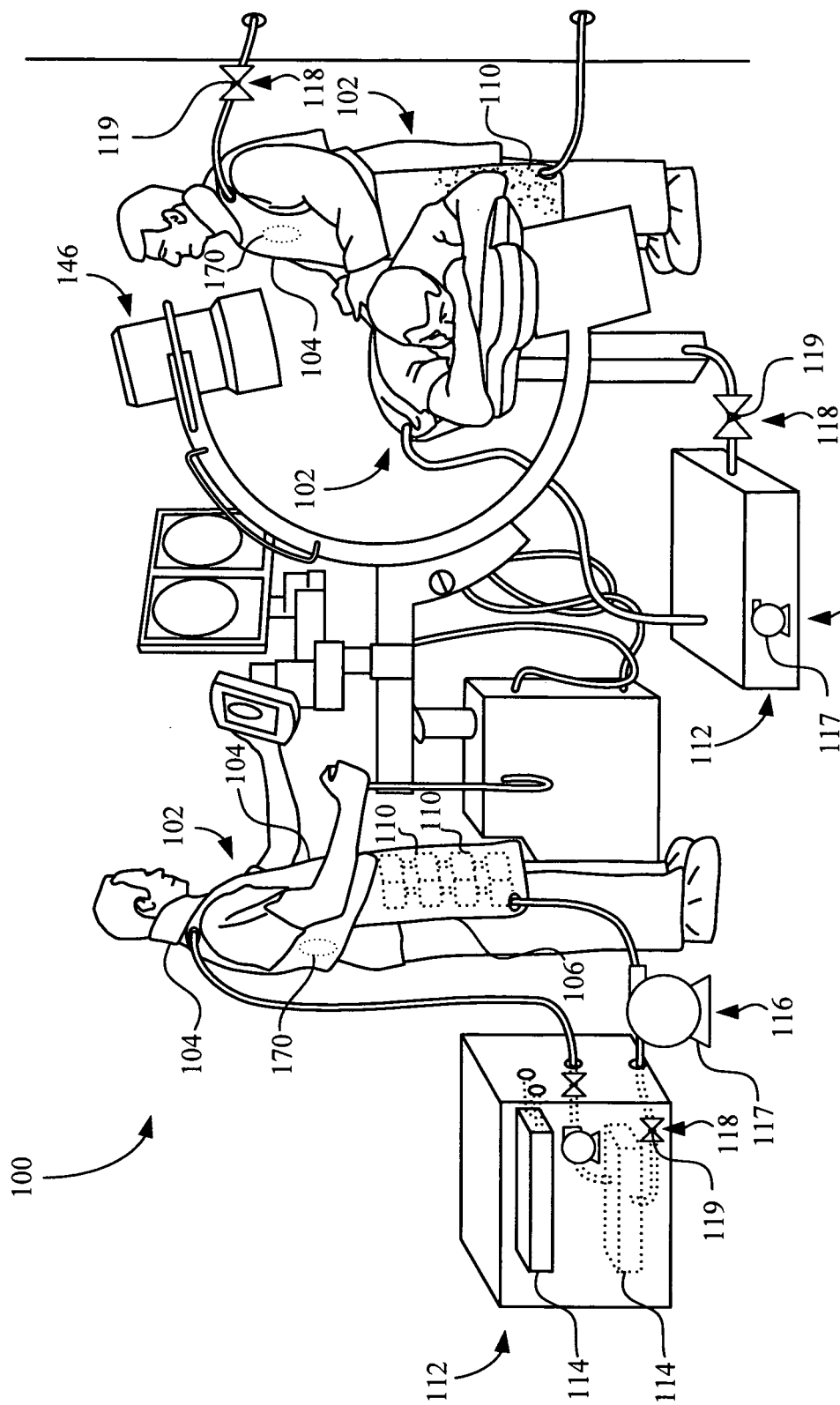
FIG. 1 is a perspective view of a system according to one embodiment.
Figure 2A:
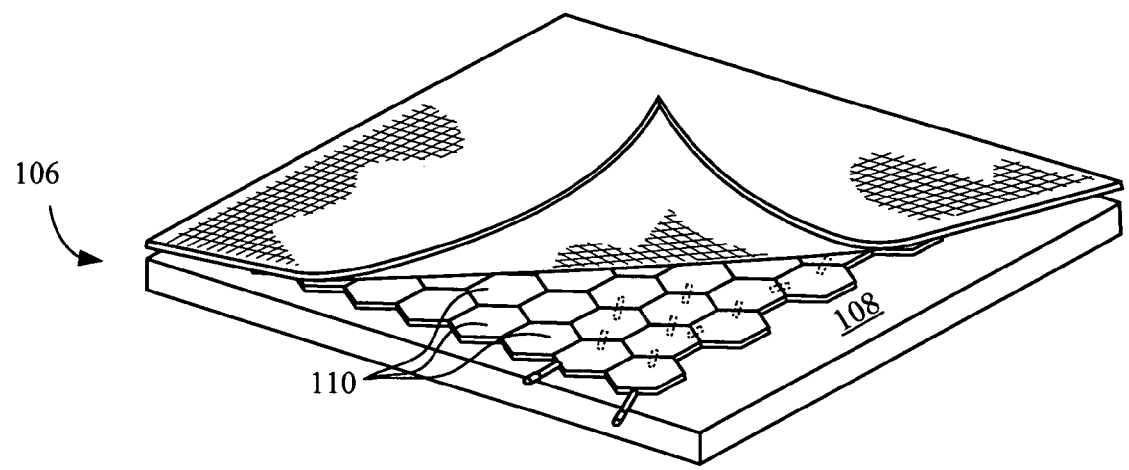
FIG. 2A is a perspective view of a system according to one embodiment.
Figure 2B:
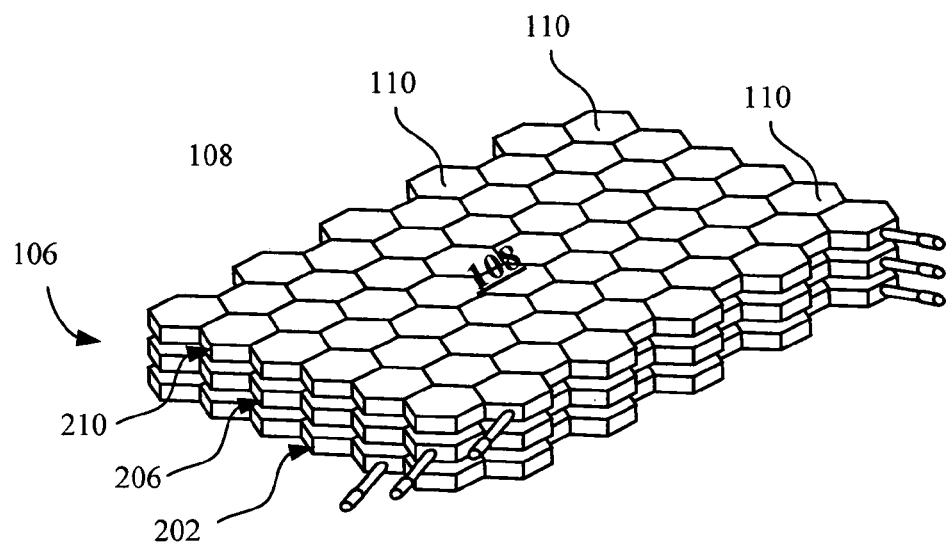
FIG. 2B is a perspective view of a system according to one embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Medical systems (e.g., fluoroscopy systems, computed tomography systems, radiography systems, radiation treatment systems, x-ray imaging system, etc.) are valuable diagnostics and treatment tools in medical practice. Likewise, cabinet x-ray systems (e.g., closed x-ray systems, x-ray inspection systems, x-ray screening systems, x-ray security systems, baggage x-ray systems, etc.) are useful tools for detection of contraband, contaminants, or manufacturing defects without damaging or destroying the item being examined.

Exposure to radiation may cause cancer (especially leukemia), birth defects in the children of exposed parents and cataracts. These health effects (excluding genetic effects) have been observed in studies of medical radiologists, uranium miners, radium workers, and radiotherapy patients who have received large doses of radiation. Studies of radiation effects on laboratory animals have provided a large body of data on radiation health effects including genetic effects. Most of the studies mentioned above involve acute exposure to high levels of radiation. Acute exposure can be, for example, exposure to hundreds of rem (Röentgen equivalent in man) within a few hours or less. Such radiation doses far exceed the occupational dose limits currently recommended (less than 5 rem per year). However, the major concerns today are about delayed health effects arising from chronic cumulative exposure to radiation.

The major health concern from chronic cumulative exposure to radiation is cancer which may appear 5 to 20 years after exposure to relatively low levels of radiation. The current limits for radiation exposure set by the FDA for adults are: 50 mSv (millisieverts) (5 rems) per year and 30 mSv (3 rems) per single dose. (http://tech.mit.edu/Bulletins/Radiation/rad5.txt). For children, who are more vulnerable to radiation, the limits are 5 mSv (0.5 rems) annually and 3 mSv (0.3 rems) per single dose. A lifetime occupational exposure level of no greater than 400 mSv (40 rems) is recommended by government agencies (Hall et al., Canadian Fam. Physician 52: 976-77, 2006). Compliance with these radiation exposure limits is complicated by the lack of cumulative radiation exposure data, especially in regard to lifetime exposure limits. Also the increased usage of computed tomography scans for medical imaging (Brenner and Hall, N. Engl. J. Med. 357: 2277-84, 2007) has created a need for monitoring, x-ray shielding, and protecting against a radiation exposure event to avoid exceeding exposure limits.

X-ray shielding fluid compositions are described with which one or more methodologies or technologies can be implemented such as, for example, providing x-ray shielding and protection. Factors affecting the radiation amount or dose received from an x-ray source include the exposure time, the distance from x-ray source, the utilization of x-ray shielding, or the like. The type and amount of material to attenuate (shield) x-ray radiation is dependent upon the energy of the x rays, the material's chemical composition, and the material's density.

In an embodiment, an x-ray shielding fluid composition includes a plurality of x-ray shielding particles and a carrier fluid. Non-limiting examples of particles include glass beads having one or more x-ray shielding agents, nanoparticles having a plurality of shielding agents within a glass material matrix, particles having a plurality of elemental dopants within a material matrix, or the like. In an embodiment, each of the x-ray shielding particles includes at least a first x-ray shielding agent and a second x-ray shielding agent. In an embodiment, the plurality of x-ray shielding particles includes a third x-ray shielding agent, the third x-ray shielding agent having one or more absorption edges different from the second x-ray shielding agent and the first x-ray shielding agent. In an embodiment, the plurality of x-ray shielding particles includes a fourth x-ray shielding agent, the fourth x-ray shielding agent having one or more absorption edges different from the third x-ray shielding agent, the second x-ray shielding agent, and the first x-ray shielding agent. In an embodiment, the plurality of x-ray shielding particles includes a fifth x-ray shielding agent, the fifth x-ray shielding agent having one or more absorption edges different from the fourth x-ray shielding agent, the third x-ray shielding agent, the second x-ray shielding agent, and the first x-ray shielding agent.

In an embodiment, the second x-ray shielding agent includes one or more absorption edges different from the first x-ray shielding agent. In an embodiment, the second x-ray shielding agent includes one or more characteristic x-ray absorption edges different from the first x-ray shielding agent. In an embodiment, the second x-ray shielding agent includes one or more k-edges, or one or more l-edges, different from the first x-ray shielding agent. In an embodiment, the second x-ray shielding agent includes an x-ray mass attenuation coefficient different from the first x-ray shielding agent. In an embodiment, the second x-ray shielding agent includes at least one k-edge having an energy level lower than at least one k-edge of the first x-ray shielding agent. In an embodiment, the second x-ray shielding agent includes at least one k-edge or l-edge corresponding to an x-ray energy absorption minimum of the first x-ray shielding agent.

In an embodiment, the plurality of x-ray shielding particles includes one or more x-ray radio-opaque materials (e.g., barium sulfate, silicon carbide, silicon nitride, alumina, zirconia, etc.). In an embodiment, the plurality of x-ray shielding particles includes one or more x-ray attenuating materials. In an embodiment, the plurality of x-ray shielding particles includes one or more x-ray attenuating ceramic materials.

In an embodiment, the plurality of x-ray shielding particles comprise one or ferromagnetic materials. Ferromagnetic materials include those materials having a Curie temperature, above which thermal agitation destroys the magnetic coupling giving rise to the alignment of the elementary magnets (electron spins) of adjacent atoms in a lattice (e.g., a crystal lattice). In an embodiment, one or more of the plurality of x-ray shielding particles include one or more ferromagnets. Among ferromagnetic materials, examples include, but are not limited to, crystalline ferromagnetic materials, ferromagnetic oxides, materials having a net magnetic moment, materials having a positive susceptibility to an external magnetic field, non-conductive ferromagnetic materials, non-conductive ferromagnetic oxides, ferromagnetic elements (e.g., cobalt, gadolinium, iron, or the like), rare earth elements, ferromagnetic metals, ferromagnetic transition metals, materials that exhibit magnetic hysteresis, and the like, and alloys or mixtures thereof.

Further examples of ferromagnetic materials include, but are not limited to, chromium (Cr), cobalt (Co), copper (Cu), dysprosium (Dy), europium (Eu), gadolinium (Gd), iron (Fe), magnesium (Mg), neodymium (Nd), nickel (Ni), yttrium (Y), and the like. Further examples of ferromagnetic materials include, but are not limited to, chromium dioxide ($CrO_2$), copper ferrite ($CuOFe_2O_3$), europium oxide (EuO), iron(II, III) oxide ($FeOFe_2O_3$), iron(III) oxide ($Fe_2O_3$), magnesium ferrite ($MgOFe_2O_3$), manganese ferrite ($MnOFe_2O_3$), nickel ferrite ($NiOFe_2O_3$), yttrium-iron-garnet ($Y_3Fe_5O_{12}$), and the like. Further examples of ferromagnetic materials include, but are not limited to, manganese arsenide (MnAs), manganese bismuth (MnBi), manganese (III) antimonide (MnSb), Mn—Zn ferrite, neodymium alloys, neodymium, Ni—Zn ferrite, and samarium-cobalt.

In an embodiment, one or more of the plurality of x-ray shielding particles include at least one iron oxide. Among iron oxides, examples include, but are not limited to, copper ferrite ($CuOFe_2O_3$), iron(II, III) oxide ($FeOFe_2O_3$), iron(III) oxide ($Fe_2O_3$), magnesium ferrite ($MgOFe_2O_3$), manganese ferrite ($MnOFe_2O_3$), nickel ferrite ($NiOFe_2O_3$), yttrium-iron-garnet ($Y_3Fe_5O_{12}$), ferric oxides, ferrous oxides, and the like. In an embodiment, one or more of the plurality of x-ray shielding particles include at least one iron oxide. Among iron oxides, examples include, but are not limited to, copper ferrite ($CuOFe_2O_3$), iron(II, III) oxide ($FeOFe_2O_3$), iron(III) oxide ($Fe_2O_3$), magnesium ferrite ($MgOFe_2O_3$), manganese ferrite ($MnOFe_2O_3$), nickel ferrite ($NiOFe_2O_3$), yttrium-iron-garnet ($Y_3Fe_5O_{12}$), ferric oxides, ferrous oxides, and the like. In an embodiment, one or more of the plurality of x-ray shielding particles are configured to include one or more magnetic components.

In an embodiment, the plurality of x-ray shielding particles comprise one or ferrimagnetic materials. In an embodiment, one or more of the plurality of x-ray shielding particles include one or more ferrimagnets (e.g., soft ferrites, hard ferrites, or the like). Among ferrimagnetic materials, examples include, but are not limited to, ferrimagnetic oxides (e.g., ferrites, garnets, or the like). Further examples of ferrimagnetic materials include ferrites with a general chemical formula of $AB_2O_4$ (e.g., $CoFe_2O_4$, $MgFe_2O_4$, $ZnFe_2O_4$) where A and B represent various metal cations. In an embodiment, A is Mg, Zn, Mn, Ni, Co, or Fe(II); B is Al, Cr(III), Mn(III) or Fe(III), and O is oxygen. In an embodiment, A is a divalent atom of radius ranging from about 80 pm to about 110 pm (e.g., Cu, Fe, Mg, Mn, Zn, or the like), B is a trivalent atom of radius ranging from about 75 pm to about 90 pm, (e.g., Al, Fe, Co, Ti, or the like), and O is oxygen. Further examples of ferrimagnetic materials include iron ferrites with a general chemical formula $MOFe_2O_3$ (e.g., $CoFe_2O_4$, $Fe_3O_4$, $MgFe_2O_4$, or the like) where M is a divalent ion such as Fe, Co, Cu, Li, Mg, Ni, or Zn.

Further examples of ferrimagnetic materials include materials having a magnetization compensation point, materials that are associated with a partial cancellation of antiferromagnetically aligned magnetic sublattices with different values of magnetic moments, or material having different temperature dependencies of magnetization. See e.g., Kageyama et al., Weak Ferrimagnetism, Compensation Point, and Magnetization Reversal in $Ni(HCOO)_2.2H_2O$, Physical Rev. B, 224422 (2003). In an embodiment, the plurality of x-ray shielding particles comprises one or more paramagnetic materials.

In an embodiment, at least one of the first x-ray shielding agent or the second x-ray shielding agent includes at least one material that absorbs x-rays at one or more frequencies and fluoresce x-rays at one or more lower frequencies. In an embodiment, at least one of the first x-ray shielding agent or the second x-ray shielding agent includes at least one of boron, molybdenum, neodymium, niobium, strontium, tungsten yttrium, or zirconium, or combinations thereof. In an embodiment, at least one of the first x-ray shielding agent or the second x-ray shielding agent includes at least one of barium sulfate ($BaSO_4$), boron nitride (BN), boron carbide ($B_4C$), boron oxide ($B_2O_3$), or barium oxide (BaO). In an embodiment, at least one of the first x-ray shielding agent or the second x-ray shielding agent includes at least one of strontium oxide (SrO), zinc oxide (ZnO), or zirconium dioxide ($ZrO_2$). In an embodiment, at least one of the first x-ray shielding agent or the second x-ray shielding agent includes one or more $SiO_2$—PbO-alkali metal oxide glasses, CaO—SrO—$B_2O_3$ glasses, or boron-lithium glasses. In an embodiment, at least one of the first x-ray shielding agent or the second x-ray shielding agent includes borated high density polyethylene. In an embodiment, at least one of the first x-ray shielding agent or the second x-ray shielding agent includes at least one of mylar ($C_{10}H_8O_4$), parylene-C($C_8H_7Cl$), parylene-N($C_8H_8$), poly(methyl methacrylate) (PMMA), polycarbonate ($C_{16}H_{14}O_3$), polyethylene, or ultra high molecular weight polyethylene. In an embodiment, at least one of the first x-ray shielding agent or the second x-ray shielding agent includes silicon nitride ($Si_3N_4$). In an embodiment, at least one of the first x-ray shielding agent or the second x-ray shielding agent includes at least one of mercury (Hg), lead (Pb), lithium fluoride (LiF), tantalum (Ta), or tungsten (W). In an embodiment, at least one of the first x-ray shielding agent or the second x-ray shielding agent includes teflon ($C_2F_4$).

In an embodiment, the carrier fluid ranges from about 1 to about 98 volume percent of the total volume of the x-ray shielding fluid composition. In an embodiment, an x-ray shielding fluid composition includes a carrier fluid including a fluid material having one or more x-ray absorption edges. In an embodiment, the carrier fluid includes a fluid material having one or more x-ray absorption edges different from the second x-ray shielding agent and the first x-ray shielding agent. In an embodiment, the carrier fluid includes a fluid material having one or more x-ray absorption edges different from the second x-ray shielding agent and the first x-ray shielding agent. In an embodiment, the carrier fluid includes a fluid that is substantially non-volatile, non-polar, or non-aqueous. In an embodiment, the carrier fluid includes mineral oil, paraffin oil, cycloparaffin oil, or synthetic hydrocarbon oil. In an embodiment, the carrier fluid includes a gas carrier. In an embodiment, the carrier fluid includes an aerosol. In an embodiment, the carrier fluid includes two or more immiscible liquids.

In an embodiment, an x-ray shielding fluid composition includes one or more anti-flocculant agents. In an embodiment, the anti-flocculant agents adsorb onto the x-ray shielding particle surface, increasing the x-ray shielding particle electrostatic repulsion. The increased electrostatic repulsion of like charged x-ray shielding particles decreases the occurrence of x-ray shielding particle aggregates. In an embodiment the addition of anti-flocculant agents enhanced stability of the x-ray shielding fluid composition. In an embodiment, at least some of the plurality of x-ray shielding particles are coated with an anti-flocculant coating.

In an embodiment, the x-ray shielding fluid composition includes at least a first x-ray shielding agent and a second x-ray shielding agent, the second x-ray shielding agent having one or more absorption edges different from the first x-ray shielding agent, and a carrier fluid. In an embodiment, the second x-ray shielding agent includes one or more characteristic x-ray absorption edges different from the first x-ray shielding agent. In an embodiment, the second x-ray shielding agent includes one or more k-edges, or one or more l-edges, different from the first x-ray shielding agent. In an embodiment, the second x-ray shielding agent includes an x-ray mass attenuation coefficient different from the first x-ray shielding agent.

In an embodiment, the second x-ray shielding agent includes at least one k-edge having an energy level lower than at least one k-edge of the first x-ray shielding agent. In an embodiment, at least one of the first x-ray shielding agent or the second x-ray shielding agent includes at least one of lead (Pb), lithium fluoride (LiF), tantalum (Ta), or tungsten (W). In an embodiment, at least one of the first x-ray shielding agent or the second x-ray shielding agent includes teflon ($C_2F_4$).

In an embodiment, the x-ray shielding fluid composition includes a third x-ray shielding agent, the third x-ray shielding agent having one or more absorption edges different from the second x-ray shielding agent and the first x-ray shielding agent. In an embodiment, the x-ray shielding fluid composition includes a fourth x-ray shielding agent, the fourth x-ray shielding agent having one or more absorption edges different from the third x-ray shielding, the second x-ray shielding agent, and the first x-ray shielding agent. In an embodiment, the x-ray shielding fluid composition includes a fifth x-ray shielding agent, the fifth x-ray shielding agent having one or more absorption edges different from the fourth x-ray shielding agent, the third x-ray shielding, the second x-ray shielding agent, and the first x-ray shielding agent.

FIGS. 1 through 4 show a dynamic x-ray shielding system 100 including one or more dynamic x-ray shielding devices 102, in which one or more methodologies or technologies can be implemented such as, for example, providing x-ray shielding, x-ray radiation protection, or the like. In an embodiment, the dynamic x-ray shielding device 102 forms part of a dynamic x-ray shielding garment 104. In an embodiment, the x-ray shielding system 100 includes one or more dynamic x-ray shielding devices 102 having at least a flexible layer 106 including a support structure 108 having a plurality of interconnected interstitial spaces 110 that provide a circulation network for an x-ray shielding fluid composition. In an embodiment, the dynamic x-ray shielding system 100 includes one or more x-ray shielding fluid reservoir assemblies 112 including one or more reservoirs 114 configured to store and supply an x-ray shielding fluid composition to or from the x-ray shielding agent reservoir 114, and along one or more of the plurality of interconnected interstitial space 110.

In an embodiment, the dynamic x-ray shielding system 100 includes one or more pump assemblies 116 including one or more pumps 117 (e.g., mechanical pumps, magnetic pumps, centrifugal pumps, diaphragm pumps, gear pumps, flexible impeller pumps, peristaltic pumps, piston pumps, rotary valve pumps, etc.) that circulates the x-ray shielding fluid composition within at least a portion of the circulation network. For example, in an embodiment, the dynamic x-ray shielding system 100 includes an x-ray shielding fluid composition pump assembly 116 that is in fluid communication with at least one of the x-ray shielding fluid reservoir assembly 112 or the circulation network and that supplies and circulates the x-ray shielding fluid composition to or from the x-ray shielding agent reservoir assembly 112, and along one or more regions within the circulation network. In an embodiment, the dynamic x-ray shielding garment 104 includes one or more pumps 117 that configured to generate magnetic forces on magnetic components of the x-ray shielding fluid composition to circulate the x-ray shielding fluid composition to or from the x-ray shielding agent reservoir assembly 112, and along one or more regions within the circulation network In an embodiment, the dynamic x-ray shielding devices 102 includes one or more pumps 117 that circulate the x-ray shielding fluid composition within at least a portion of the circulation network. In an embodiment, the dynamic x-ray shielding system 100 includes one or more flow valve assemblies 118, including one or more flow valves 119, that are selectively actuatable between an open state which permits fluid flow through the one or more valve assemblies 118 such that the x-ray shielding fluid composition flows from the x-ray shielding fluid reservoir assembly 112 along at least a portion of a flow path, and a restrict state which restricts fluid flow through the assembly 118.

In an embodiment, the dynamic x-ray shielding system 100 includes one or more flow valves 119 to selectively direct flow of the x-ray shielding fluid composition to or from the x-ray shielding agent reservoir 114. In an embodiment, the dynamic x-ray shielding system 100 includes one or more flow valves 119 to selectively direct flow of the x-ray shielding fluid composition within the circulation network.

Figure 5:
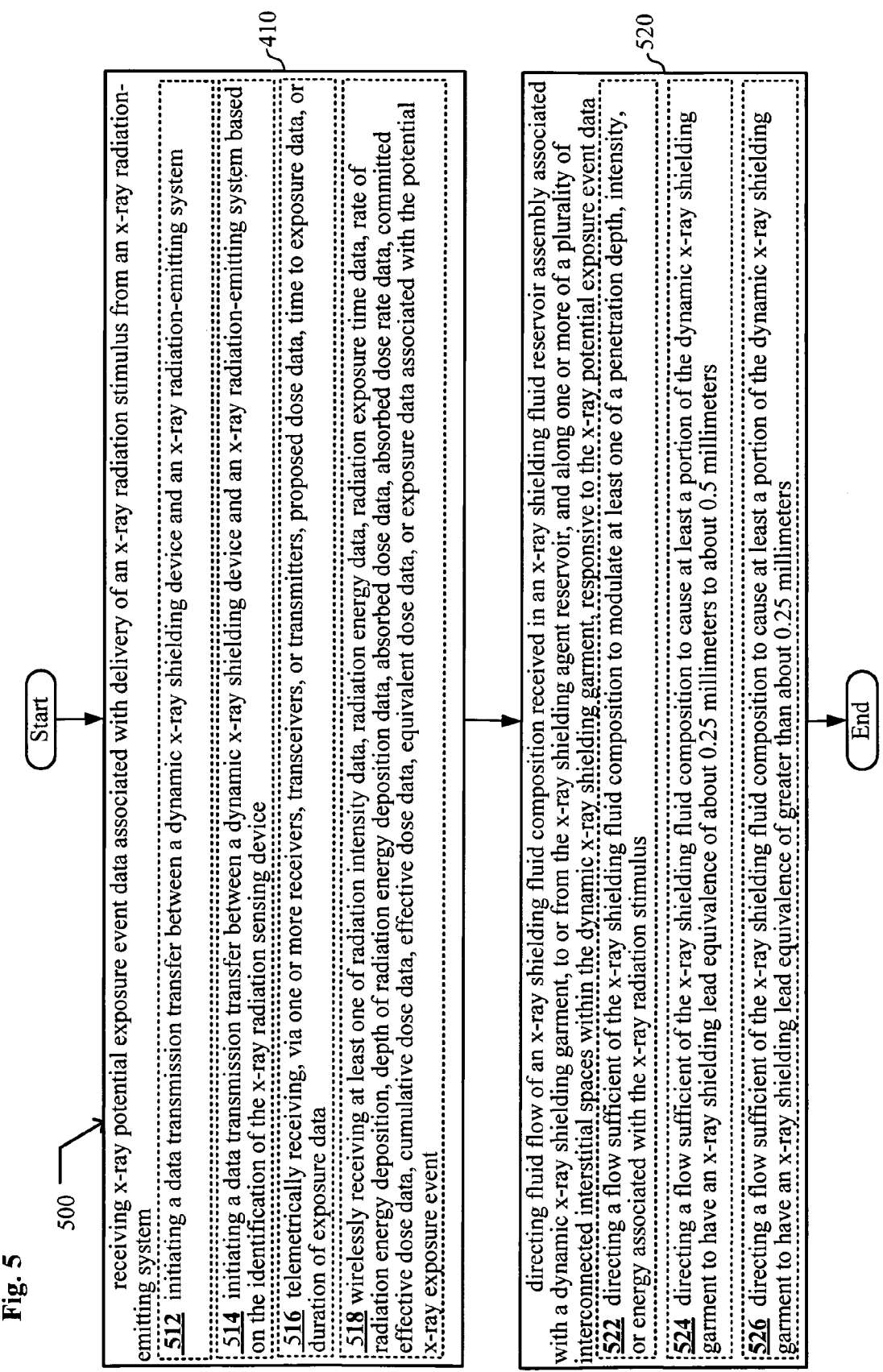
FIG. 5 shows a flow diagram of a method according to one embodiment.

In an embodiment, dynamic x-ray shielding devices 102 includes support structure 108 configured to constrain the x-ray shielding fluid composition to move along one or more of the plurality of interconnected interstitial spaces 110. In an embodiment, the support structure 108 defines one or more tubular structures (e.g., as shown in FIG. 5) forming part of the plurality of interconnected interstitial spaces 110 that provide the circulation network for the x-ray shielding fluid composition. In an embodiment, the support structure 108 comprises one or more x-ray shielding agents. In an embodiment, the support structure 108 comprises one or more x-ray radio-opaque materials. In an embodiment, the support structure 108 comprises one or more x-ray attenuating materials. In an embodiment, the support structure 108 comprises one or more x-ray attenuating ceramic materials.

Figure 3:
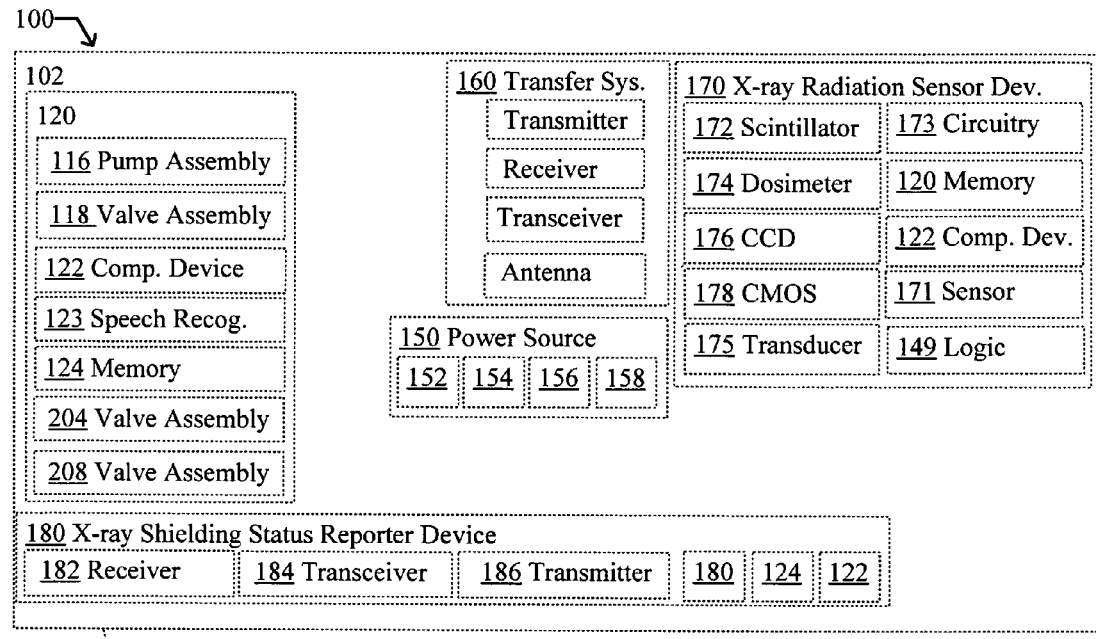
FIG. 3 is a perspective view of a system according to one embodiment.
Figure 3:
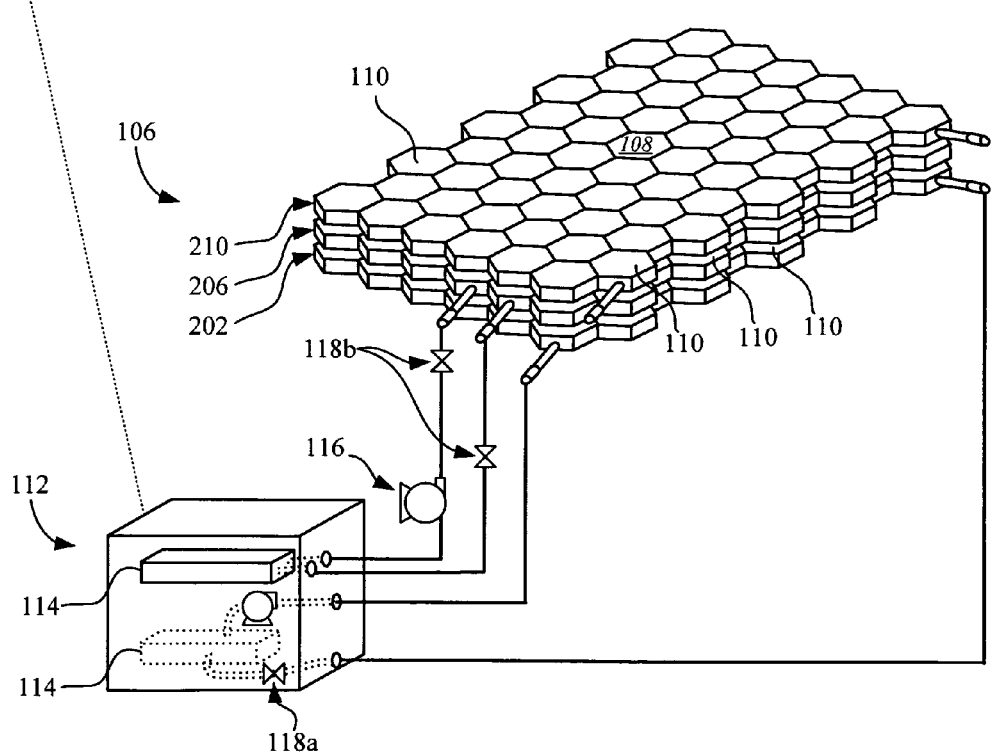
Figure 4:
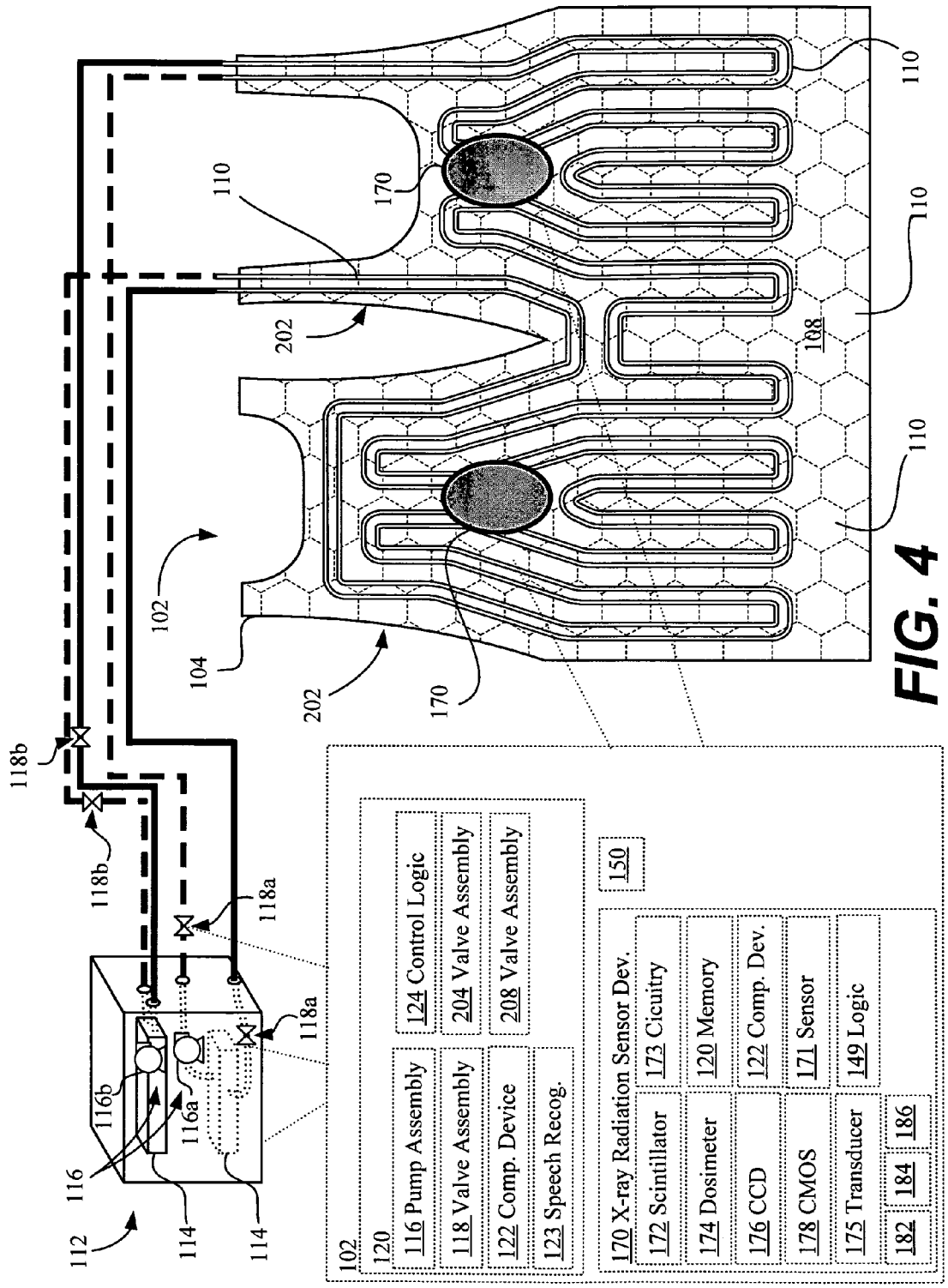
FIG. 4 is a perspective view of a system according to one embodiment.

Referring to FIG. 3, in an embodiment, the dynamic x-ray shielding device 102 includes at least a first layer 202 including one on more flow paths in fluid communication with the x-ray shielding fluid reservoir assembly 112 and configured to receive a first x-ray shielding fluid composition. Flow paths can take a variety of shapes, configurations, and geometric forms including regular or irregular forms and can have a cross-section of substantially any shape including, among others, circular, triangular, square, rectangular, polygonal, regular or irregular shapes, or the like, as well as other symmetrical and asymmetrical shapes, or combinations thereof. In an embodiment, the flow paths includes one or more interstitial spaces configured to receive the x-ray shielding fluid composition, and to provide the circulation network for the x-ray shielding fluid composition.

In an embodiment, the first flow path includes a first flow valve assembly 108a selectively actuatable between an open state which permits fluid flow through the first flow valve assembly 108a such that the first x-ray shielding fluid composition flows from the x-ray shielding fluid reservoir assembly 112 along at least a portion of the first flow path, and a restrict state which restricts fluid flow through the first flow valve assembly 108a and along the first flow path.

In an embodiment, the dynamic x-ray shielding device 102 includes a second layer 206 including a second flow path in fluid communication with the x-ray shielding fluid reservoir assembly 112 and configured to receive the second x-ray shielding fluid composition, the second flow path including a second flow valve assembly 118b selectively actuatable between an open state which permits fluid flow through the second flow valve assembly 118b such that the second x-ray shielding fluid composition flows from the x-ray shielding fluid reservoir assembly 112 along at least a portion of the first flow path, and a restrict state which restricts fluid flow through the second flow valve assembly 118b.

In an embodiment, the dynamic x-ray shielding device 102 includes a third layer 210 including a third flow path in fluid communication with the x-ray shielding fluid reservoir assembly 112 and configured to receive the third x-ray shielding fluid composition, the third flow path including a third flow valve assembly selectively actuatable between an open state which permits fluid flow through the third flow valve assembly such that the third x-ray shielding fluid composition flows from the x-ray shielding fluid reservoir assembly 112 along at least a portion of the first flow path, and a restrict state which restricts fluid flow through the third flow valve assembly.

In an embodiment, at least one of the first flow path or the second flow path includes one or more tubular structures. In an embodiment, at least one of the first flow path or the second flow path includes one or more recirculation tubular structures in fluid communication with the x-ray shielding fluid reservoir assembly 112 and operable to distribute at least one of the first x-ray shielding fluid composition or the second x-ray shielding fluid composition through at least a portion of the first flow path or the second flow path. In an embodiment, at least one of the first layer 202 or the second layer 206 comprises one or more x-ray shielding agents. In an embodiment, at least one of the first layer 202 or the second layer 206 comprises one or more x-ray radio-opaque materials. In an embodiment, at least one of the first layer 202 or the second layer 206 comprises one or more x-ray attenuating materials. In an embodiment, at least one of the first layer 202 or the second layer 206 comprises one or more x-ray attenuating ceramic materials.

In an embodiment, the dynamic x-ray shielding system 100 includes one or more x-ray shielding fluid reservoirs 114 configured to store and supply at least a first x-ray shielding fluid composition and a second x-ray shielding fluid composition. In an embodiment, the dynamic x-ray shielding device 102 includes at least one x-ray shielding fluid reservoir assembly 112 including one or more x-ray shielding fluid reservoirs 114. In an embodiment, the x-ray shielding fluid reservoir assembly 112 is structured and arranged to hold the x-ray shielding fluid composition and to selectively enable fluid communication between one or more x-ray shielding fluid reservoirs and the plurality of interconnected interstitial spaces 110.

In an embodiment, the dynamic x-ray shielding garment 104 includes an x-ray shielding fluid supply controller 120 that is operable to manage fluid flow of the x-ray shielding fluid composition to or from the x-ray shielding agent reservoir assembly 112, and along one or more of the plurality of interconnected interstitial space 110. In an embodiment, the one or more x-ray shielding fluid reservoirs 114 include at least a first x-ray shielding fluid composition and a second x-ray shielding fluid composition. In an embodiment, the second x-ray shielding fluid composition comprises one or more x-ray shielding agents different from those of the first x-ray shielding fluid composition. In an embodiment, the second x-ray shielding fluid composition comprises one or more x-ray shielding agents having one or more absorption edges different from those of the first x-ray shielding fluid composition. In an embodiment, the second x-ray shielding fluid composition comprises one or more x-ray shielding agents having one or more characteristic x-ray absorption edges different from those of the first x-ray shielding fluid composition.

In an embodiment, the one or more x-ray shielding fluid reservoirs 114 include at least a first x-ray shielding fluid composition and a second x-ray shielding fluid composition, the second x-ray shielding fluid composition comprises one or more x-ray shielding agents having one or more k-edges, or one or more l-edges, different from those of the first x-ray shielding fluid composition. In an embodiment, the second x-ray shielding fluid composition comprises one or more x-ray shielding agents having one or more x-ray mass attenuation coefficients different from those of the first x-ray shielding fluid composition. In an embodiment, the second x-ray shielding fluid composition comprises one or more x-ray shielding agents having at least one k-edge having an energy level lower than at least one k-edge of the first x-ray shielding fluid composition. In an embodiment, the second x-ray shielding fluid composition comprises one or more x-ray shielding agents different from those of the second x-ray shielding fluid composition and the first x-ray shielding fluid composition.

In an embodiment, the one or more x-ray shielding fluid reservoirs 114 include an x-ray shielding fluid composition having a plurality of x-ray shielding particles, each including one or more x-ray shielding agents, and a carrier fluid. In an embodiment, the plurality of x-ray shielding particles includes one or more x-ray radio-opaque materials. In an embodiment, the plurality of x-ray shielding particles includes one or more x-ray attenuating materials. In an embodiment, the plurality of x-ray shielding particles includes one or more x-ray attenuating ceramic materials. In an embodiment, the plurality of x-ray shielding particles includes one or more x-ray absorbers. In an embodiment, the plurality of x-ray shielding particles include one or more x-ray scattering materials. In an embodiment, at least one of the first x-ray shielding agent or the second x-ray shielding agent includes at least one of boron, molybdenum, neodymium, niobium, strontium, tungsten yttrium, or zirconium, or combinations thereof.

In an embodiment, at least one of the first x-ray shielding agent or the second x-ray shielding agent includes at least one of barium sulfate ($BaSO_4$), boron nitride (BN), boron carbide ($B_4C$), boron oxide ($B_2O_3$), or barium oxide (BaO). In an embodiment, at least one of the first x-ray shielding agent or the second x-ray shielding agent includes at least one of strontium oxide (SrO), zinc oxide (ZnO), or zirconium dioxide ($ZrO_2$). In an embodiment, at least one of the first x-ray shielding agent or the second x-ray shielding agent includes one or more $SiO_2$—PbO-alkali metal oxide glasses, CaO—SrO—$B_2O_3$ glasses, or boron-lithium glasses. In an embodiment, at least one of the first x-ray shielding agent or the second x-ray shielding agent includes borated high density polyethylene. In an embodiment, at least one of the first x-ray shielding agent or the second x-ray shielding agent includes at least one of mylar ($C_{10}H_8O_4$), parylene-C($C_8H_7Cl$), parylene-N($C_8H_8$), poly(methyl methacrylate) (PMMA), polycarbonate ($C_{16}H_{14}O_3$), polyethylene, or ultra high molecular weight polyethylene. In an embodiment, at least one of the first x-ray shielding agent or the second x-ray shielding agent includes silicon nitride ($Si_3N_4$). In an embodiment, at least one of the first x-ray shielding agent or the second x-ray shielding agent includes at least one of lead (Pb), lithium fluoride (LiF), tantalum (Ta), or tungsten (W). In an embodiment, at least one of the first x-ray shielding agent or the second x-ray shielding agent includes teflon ($C_2F_4$). In an embodiment, at least one of the first x-ray shielding agent or the second x-ray shielding agent includes lead (II) oxide (PbO). In an embodiment, the carrier fluid comprises about 1 to about 98 volume percent of the total volume of the x-ray shielding fluid composition.

In an embodiment, the one or more x-ray shielding fluid reservoirs 114 include an x-ray shielding fluid composition having a plurality of x-ray shielding particles, each having at least a first x-ray shielding agent and a second x-ray shielding agent, the second x-ray shielding agent having one or more absorption edges different from the first x-ray shielding agent, and a carrier fluid. In an embodiment, the second x-ray shielding agent includes one or more characteristic x-ray absorption edges different from the first x-ray shielding agent. In an embodiment, the second x-ray shielding agent includes one or more k-edges, or one or more l-edges, different from the first x-ray shielding agent. In an embodiment, the second x-ray shielding agent includes an x-ray mass attenuation coefficient different from the first x-ray shielding agent. In an embodiment, the second x-ray shielding agent includes at least one k-edge having an energy level lower than at least one k-edge of the first x-ray shielding agent. In an embodiment, the one or more x-ray shielding fluid reservoirs 114 include an x-ray shielding fluid composition having a plurality of x-ray shielding particles having at least a third x-ray shielding agent, the third x-ray shielding agent having one or more absorption edges different from the second x-ray shielding agent and the first x-ray shielding agent. In an embodiment, the one or more x-ray shielding fluid reservoirs 114 include an x-ray shielding fluid composition having a plurality of x-ray shielding particles having at least a fourth x-ray shielding agent, the fourth x-ray shielding agent having one or more absorption edges different from the third x-ray shielding agent, the second x-ray shielding agent, and the first x-ray shielding agent. In an embodiment, the one or more x-ray shielding fluid reservoirs 114 include an x-ray shielding fluid composition having a plurality of x-ray shielding particles having at least a fifth x-ray shielding agent, the fifth x-ray shielding agent having one or more absorption edges different from the fourth x-ray shielding agent, the third x-ray shielding agent, the second x-ray shielding agent, and the first x-ray shielding agent.

In an embodiment, the one or more x-ray shielding fluid reservoirs 114 include an x-ray shielding fluid composition having at least a first x-ray shielding agent and a second x-ray shielding agent, the second x-ray shielding agent having one or more absorption edges different from the first x-ray shielding agent, and a carrier fluid. In an embodiment, the second x-ray shielding agent includes one or more characteristic x-ray absorption edges different from the first x-ray shielding agent. In an embodiment, the second x-ray shielding agent includes one or more k-edges, or one or more l-edges, different from the first x-ray shielding agent. In an embodiment, the second x-ray shielding agent includes an x-ray mass attenuation coefficient different from the first x-ray shielding agent. In an embodiment, the second x-ray shielding agent includes at least one k-edge having an energy level lower than at least one k-edge of the first x-ray shielding agent. In an embodiment, at least one of the first x-ray shielding agent or the second x-ray shielding agent includes at least one of mercury (Hg), lead (Pb), lithium fluoride (LiF), tantalum (Ta), or tungsten (W). In an embodiment, at least one of the first x-ray shielding agent or the second x-ray shielding agent includes teflon ($C_2F_4$).

In an embodiment, the one or more x-ray shielding fluid reservoirs 114 include an x-ray shielding fluid composition having a third x-ray shielding agent, the third x-ray shielding agent having one or more absorption edges different from the second x-ray shielding agent and the first x-ray shielding agent. In an embodiment, the one or more x-ray shielding fluid reservoirs 114 include an x-ray shielding fluid composition having a fourth x-ray shielding agent, the fourth x-ray shielding agent having one or more absorption edges different from the third x-ray shielding, the second x-ray shielding agent, and the first x-ray shielding agent: In an embodiment, the one or more x-ray shielding fluid reservoirs 114 include an x-ray shielding fluid composition having a fifth x-ray shielding agent, the fifth x-ray shielding agent having one or more absorption edges different from the fourth x-ray shielding agent, the third x-ray shielding, the second x-ray shielding agent, and the first x-ray shielding agent.

In an embodiment, the dynamic x-ray shielding system 100 includes an x-ray shielding fluid supply controller 120 associated with one or more flow valve assemblies 116 and configured to selectively actuate the one or more flow valve assemblies 118 to regulate fluid flow of a defined quantity of x-ray shielding fluid composition from one or more reservoirs 114, through the one or more flow valve assemblies 118, into the at least a portion of the circulation network. For example, in an embodiment, the dynamic x-ray shielding system 100 includes an x-ray shielding fluid supply controller 120 associated with at least the first flow valve assembly 108a and the second flow valve assembly 118*b* and configured to selectively actuate the first or the second flow valve assembly 118*b* to regulate fluid flow of a defined quantity of at least one of the first x-ray shielding fluid composition or the second x-ray shielding fluid composition from the reservoir, through at least one of the first flow valve or the second flow valve, into the at least a portion of the first flow path or the second flow path.

In an embodiment, the x-ray shielding fluid supply controller 120 includes, among other things, one or more computing devices 122 such as a processor (e.g., a microprocessor), a central processing unit (CPU), a digital signal processor (DSP), an application-specific integrated circuit (ASIC), a field programmable gate array (FPGA), or the like, or any combinations thereof. For example, in an embodiment, the x-ray shielding fluid supply controller 120 includes one or more computing devices 122 operably couple to at least one of an x-ray shielding fluid composition pump assembly 116 or a flow valve assembly 118 and configured to actuate at least one of the x-ray shielding fluid composition pump assembly 116 or the flow valve assembly 118.

In an embodiment, the x-ray shielding fluid supply controller 120 includes one or more computing devices 122 operably couple to at least one flow valve assembly 118 and is configured to actuate the flow valve assembly 118 between an open state which permits fluid flow through the flow valve assembly 118 such that an x-ray shielding fluid composition flows from the x-ray shielding fluid reservoir assembly 112 along at least a portion of a flow path, and a restrict state which restricts fluid flow through the flow valve assembly 118. In an embodiment, the x-ray shielding fluid supply controller 120 includes discrete digital or analog circuit elements or electronics, or combinations thereof. In an embodiment, the x-ray shielding fluid supply controller 120 includes one or more ASICs having a plurality of predefined logic components. In an embodiment, the x-ray shielding fluid supply controller 120 includes one or more FPGA having a plurality of programmable logic components.

In an embodiment, the x-ray shielding fluid supply controller 120 includes one or more components operably coupled (e.g., communicatively, electromagnetically, magnetically, ultrasonically, optically, inductively, electrically, capacitively coupled, or the like) to each other. In an embodiment, the x-ray shielding fluid supply controller 120 includes one or more remotely located components. In an embodiment, remotely located components are operably coupled via wireless communication. In an embodiment, remotely located components are operably coupled via one or more receivers 182, transceivers 184, or transmitters 186, or the like.

In an embodiment, the x-ray shielding fluid supply controller 120 includes one or more memory devices 124 that, for example, store flow control instructions or data. Non-limiting examples of one or more memory devices 124 include volatile memory (e.g., Random Access Memory (RAM), Dynamic Random Access Memory (DRAM), or the like), non-volatile memory (e.g., Read-Only Memory (ROM), Electrically Erasable Programmable Read-Only Memory (EEPROM), Compact Disc Read-Only Memory (CD-ROM), or the like), persistent memory, or the like. Further non-limiting examples of one or more memory devices 124 include Erasable Programmable Read-Only Memory (EPROM), flash memory, or the like. The one or more memory devices 124 can be coupled to, for example, one or more computing devices 122 by one or more instructions, data, or power buses.

In an embodiment, the x-ray shielding fluid supply controller 120 includes one or more computer-readable media drives, interface sockets, Universal Serial Bus (USB) ports, memory card slots, or the like, and one or more input/output components such as, for example, a graphical user interface, a display, a keyboard, a keypad, a trackball, a joystick, a touch-screen, a mouse, a switch, a dial, or the like, and any other peripheral device. In an embodiment, the x-ray shielding fluid supply controller 120 includes one or more user input/output components that are operably coupled to at least one computing device 122 to control (electrical, electromechanical, software-implemented, firmware-implemented, or other control, or combinations thereof) at least one parameter associated with, for example, determining an exposure status of a user in response to one or more transcutaneously received x-ray radiation stimuli obtained via the implantable radiation sensing device 102.

In an embodiment, the x-ray shielding fluid supply controller 120 includes a computer-readable media drive or memory slot configured to accept signal-bearing medium (e.g., computer-readable memory media, computer-readable recording media, or the like). In an embodiment, a program for causing a system to execute any of the disclosed methods can be stored on, for example, a computer-readable recording medium (CRMM), a signal-bearing medium, or the like. Non-limiting examples of signal-bearing media include a recordable type medium such as a magnetic tape, floppy disk, a hard disk drive, a Compact Disc (CD), a Digital Video Disk (DVD), Blu-Ray Disc, a digital tape, a computer memory, or the like, as well as transmission type medium such as a digital and/or an analog communication medium (e.g., a fiber optic cable, a waveguide, etc.), a wired communications link, a wireless communication link (e.g., receiver 182, transceiver 184, transmitter 186, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, or the like.

In an embodiment, the x-ray shielding fluid supply controller 120 includes circuitry having one or more modules optionally operable for communication with one or more input/output components that are configured to relay user output and/or input. In an embodiment, a module includes one or more instances of electrical, electromechanical, software-implemented, firmware-implemented, or other control devices. Such devices include one or more instances of memory 120, computing devices 122, antennas, power or other supplies, logic modules or other signaling modules, gauges or other such active or passive detection components, piezoelectric transducers, shape memory elements, micro-electro-mechanical system (MEMS) elements, or other actuators.

In an embodiment, the dynamic x-ray shielding system 100 includes an x-ray shielding fluid supply controller 120 associated with at least the first flow valve assembly 108*a* and the second flow valve assembly 118*b* and configured to selectively actuate the first or the second flow valve assembly 118*b* to regulate fluid flow of a defined quantity of at least one of the first x-ray shielding fluid composition or the second x-ray shielding fluid composition from the reservoir, through at least one of the first flow valve or the second flow valve, into the at least a portion of the first flow path or the second flow path. In an embodiment, the x-ray shielding fluid supply controller 120 is operable to actuate fluid flow of the first x-ray shielding fluid composition or the second x-ray shielding fluid, received in the x-ray shielding fluid reservoir assembly 112, to or from the x-ray shielding agent reservoir and along respectively one of the first flow path or the second flow path.

In an embodiment, the x-ray shielding fluid supply controller 120 is operable to actuate concurrent or sequential fluid flow of the first x-ray shielding fluid composition or the second x-ray shielding fluid, received in the x-ray shielding fluid reservoir assembly 112, to or from the x-ray shielding agent reservoir and along respectively one of the first flow path or the second flow path. In an embodiment, then x-ray shielding fluid supply controller 120 includes control logic 149 arranged to determine an actuate flow condition and to actuate the flow of the first x-ray shielding fluid composition or the second x-ray shielding fluid, received in the x-ray shielding fluid reservoir assembly 112, to or from the x-ray shielding agent reservoir and along respectively one of the first flow path or the second flow path, responsive to the actuate flow condition.

In an embodiment, then x-ray shielding fluid supply controller 120 includes control logic 149 arranged to determine an actuate flow condition and to actuate the flow of the first x-ray shielding fluid composition or the second x-ray shielding fluid, received in the x-ray shielding fluid reservoir assembly 112, to or from the x-ray shielding agent reservoir and along respectively one of the first flow path or the second flow path, responsive to at least one of an authorization protocol, an authentication protocol, or an activation protocol. In an embodiment, the x-ray shielding fluid supply controller 120 includes a speech recognition module 123 that causes the x-ray shielding fluid supply controller 120 to modulate the flow of the first x-ray shielding fluid composition or the second x-ray shielding fluid, received in the x-ray shielding fluid reservoir assembly 112, to or from the x-ray shielding agent reservoir 114 and along respective one of the first flow path or the second flow path 210, responsive to one or more audio inputs.

In an embodiment, the dynamic x-ray shielding system 100 includes a power source 150 including at least one of a thermoelectric generator 152, a piezoelectric generator 154, a microelectromechanical system generator 156, or a biomechanical-energy harvesting generator 158. In an embodiment, the dynamic x-ray shielding system 100 includes a power source 150 electromagnetically, magnetically, ultrasonically, optically, inductively, electrically, or capacitively coupled to the x-ray shielding fluid supply controller 120. In an embodiment, the dynamic x-ray shielding system 100 includes an energy transfer system 160 electromagnetically, magnetically, ultrasonically, optically, inductively, electrically, or capacitively coupled to the x-ray shielding fluid supply controller 120.

In an embodiment, the dynamic x-ray shielding system 100 includes one or more x-ray radiation sensor devices 170. In an embodiment, the one or more x-radiation sensing devices 170 are operable to detect (e.g., assess, calculate, evaluate, determine, gauge, measure, monitor, quantify, resolve, sense, or the like) an incident x-ray radiation. In an embodiment, during operation, the x-ray radiation sensor devices 170 detects at least one of an actual or a potential exposure event and alerts the dynamic x-ray shielding devices 102, or the x-ray shielding fluid supply controller 120, to check whether the dynamic x-ray shielding devices 102 is activated or functional to shield or protect the user. In an embodiment, during operation, the x-ray radiation sensor devices 170 detects at least one of an actual or a potential exposure event and alerts the dynamic x-ray shielding devices 102, or the x-ray shielding fluid supply controller 120, to activate the flow of the x-ray shielding fluid composition to or from the one or more x-ray shielding fluid reservoirs and along one or more of the plurality of interconnected interstitial spaces.

In an embodiment, the dynamic x-ray shielding devices 102 includes one or more an x-ray radiation sensor devices 170 operably coupled to the x-ray shielding fluid supply controller 120. In an embodiment, the radiation sensing device 170 is operable to detect at least one characteristic (e.g., a fundamental characteristic, a spectral characteristic, a spectral signature, a physical quantity, an absorption coefficient, or the like) associated with an x-ray radiation exposure event.

In an embodiment, the dynamic x-ray shielding device 102 includes one or more x-ray radiation sensor devices 170 disposed on a user-side of the first layer that acquire at least a portion of penetrating x-ray radiation stimulus and transduce the penetrating x-ray radiation stimulus acquired by the x-ray radiation sensor device 170 into at least one measurand indicative of an x-ray flux throughput during an integration period of the one or more x-ray radiation sensor devices 170. Non-limiting examples of x-ray radiation sensor devices 170 include scintillators 172 (e.g., inorganic scintillators, thallium doped cesium iodide scintillators, scintillator-photodiode pairs, scintillation detection devices, etc.), dosimeters 174 (e.g., x-ray dosimeters, thermoluminescent dosimeters, etc.), optically stimulated luminescence detectors, photodiode arrays, charge-coupled devices (CCDs) 176, complementary metal-oxide-semiconductor (CMOS) devices 178, or the like. In an embodiment, the x-ray radiation sensor device 170 includes one or more x-ray radiation fluoroscopic elements. In an embodiment, the x-ray radiation sensor device 170 includes one or more phosphorus doped elements (e.g., ZnCdS:Ag phosphorus doped elements). In an embodiment, the x-ray radiation sensor device includes one or more amorphous silicon thin-film transistor arrays. In an embodiment, the x-ray radiation sensor device includes one or more phosphors.

In an embodiment, the x-ray radiation sensor device 170 includes one or more transducers 175 that detect and convert x-rays into electronic signals. For example, in an embodiment, the x-ray radiation sensor device 170 includes one or more x-ray radiation scintillation crystals. In an embodiment, the x-ray radiation sensor device 170 includes one or more thallium doped cesium iodide crystals (e.g., cesium iodide crystals doped with thallium CsI(Tl)). In an embodiment, during operation, the x-ray radiation sensor device's 170 computing device 122 processes the electronic signals generated by the one or more transducers 175 to determine one or more of intensity, energy, time of exposure, date of exposure, exposure duration, rate of energy deposition, depth of energy deposition, or the like associated with each x-ray detected. In an embodiment, during operation, incident x-ray radiation interacts with one or more detector crystalline materials (e.g., cadmium zinc telluride, etc.) within the x-ray radiation sensor device 170, which results in the generation of a current indicative of, for example, the energy of the incident x-ray radiation.

In an embodiment, the radiation sensing device 170 includes circuitry 173 configured to, for example, detect x-ray radiation, determine exposure information based on one or more measurands, or the like. For example, in an embodiment, the x-ray radiation sensor device 170 includes at least one computing device 122 operably coupled to one or more sensors 171 that measure at least one of intensity data, energy, exposure time, rate of energy deposition, or depth of energy deposition associated with an x-ray radiation stimulus. In an embodiment, the x-ray radiation sensor device 170 includes at least one of a photodiode array, a scintillator, a thermoluminescent dosimeter, an x-ray radiation fluoroscopic element, or an amorphous silicon thin-film transistor array (e.g., amorphous silicon, thin-film transistor, active matrix array, etc.) operably coupled to at least one computing device 122.

In an embodiment, at least one of the x-ray radiation sensor devices 170 is configured to detect an x-ray radiation stimulus associated with an x-ray radiation-emitting system 146 (e.g., a medical systems, a cabinet x-ray system, closed x-ray systems, x-ray inspection systems, x-ray screening systems, x-ray security systems, baggage x-ray systems, etc.) and to generate at least one measurand indicative of an x-ray radiation exposure event during an integration period of the x-ray radiation sensor device 170. For example, during operation, in an embodiment, the x-ray radiation sensor devices 170 associated with a dynamic x-ray shielding device 102 alerts the dynamic x-ray shielding device 102 of the actual or prospective x-ray exposure event. In response, in an embodiment, a dynamic x-ray shielding device 102 (via one or more x-ray shielding fluid supply controller 120) activates the flow of an x-ray shielding fluid composition to one or more region of dynamic x-ray shielding device 102 to provide x-ray shielding and protection.

In an embodiment, the x-ray radiation sensor device 170 includes one or more pixels that acquire at least a portion of an x-ray radiation stimulus and transduces the x-ray radiation stimulus acquired by the x-ray radiation sensor device 170 into at least one measurand indicative of an x-ray radiation exposure during an integration period of the x-ray radiation sensor device 170. In an embodiment, the x-ray radiation sensor device 170 includes at least one charge-coupled device 176, complementary metal-oxide-semiconductor device 178, or a scintillation detection device. In an embodiment, the x-ray radiation sensor device 170 includes at least one of a photodiode array, a scintillator 172, a thermoluminescent dosimeter, an x-ray radiation fluoroscopic element, or an amorphous silicon thin-film transistor array. In an embodiment, the x-ray radiation sensor device 170 includes at least one computing device 122 operably coupled to one or more sensors 171 configured to acquire at least one of intensity data, x-ray energy, exposure time, rate of energy deposition, or depth of energy deposition associated with the x-ray radiation stimulus.

In an embodiment, the dynamic x-ray shielding system 100 includes an x-ray radiation sensor device 170 operable to detect at least one x-ray radiation exposure event. In an embodiment, the dynamic x-ray shielding system 100 an x-ray radiation sensor device 170 operable to determine an x-ray shielding status of the dynamic x-ray shielding device 102 by detecting the presence or absence of x-ray shielding fluid composition within one or more regions of the dynamic x-ray shielding device 102. In an embodiment, the x-ray shielding fluid supply controller 120 actuates at least one of a pump assembly 116 or a flow valve assembly 118 to actuate fluid flow of an x-ray shielding fluid composition, received in the one or more x-ray shielding fluid reservoirs 114, to or from the one or more x-ray shielding fluid reservoirs 114 and along one or more of the plurality of interconnected interstitial spaces 110 responsive to an output from the x-ray radiation sensor device 170 indicative of the x-ray radiation exposure event, a lack of x-ray shielding fluid composition in a region of the dynamic x-ray shielding device 102, the incorrect shield agent, or the like.

FIG. 5 shows a dynamic x-ray shielding garment 104 in which one or more methodologies or technologies can be implemented such as, for example, detecting an x-ray radiation stimulus, providing x-ray shielding, providing x-ray radiation protection, or the like. In an embodiment, the dynamic x-ray shielding garment 104 includes an x-ray shielding fluid reservoir assembly 112 including a plurality of reservoirs 114 configured to store and supply at least a first x-ray shielding fluid composition and a second x-ray shielding fluid composition. In an embodiment, a dynamic x-ray shielding garment 104 includes at least a first layer 202 including a first flow path in fluid communication with the x-ray shielding fluid reservoir assembly 112 and configured to receive the first x-ray shielding fluid composition.

In an embodiment, the first flow path includes first flow valve assembly 118a selectively actuatable between an open state which permits fluid flow through the first flow valve assembly 118a such that the first x-ray shielding fluid composition flows from the x-ray shielding fluid reservoir assembly along at least a portion of the first flow path, and a restrict state which restricts fluid flow through the first flow valve assembly 118a. In an embodiment, the first layer 202 includes an x-ray source side and a user protection side, and wherein the x-ray radiation sensor device 170 is located on the x-ray source of the first layer 202 so as to determine an incident x-ray flux. In an embodiment, the first layer 202 includes an x-ray source side and a user protection side. In an embodiment, the x-ray radiation sensor device 170 is located on the user protection side so as to determine an x-ray flux through the dynamic x-ray shielding garment 104.

In an embodiment, a dynamic x-ray shielding garment 104 includes a second layer 206 including a second flow path in fluid communication with the x-ray shielding fluid reservoir assembly 112 and configured to receive the second x-ray shielding fluid composition, the second flow path including a second flow valve assembly 118b selectively actuatable between an open state which permits fluid flow through the second flow valve assembly 118b such that the second x-ray shielding fluid composition flows from the x-ray shielding fluid reservoir assembly 112 along at least a portion of the first flow path, and a restrict state which restricts fluid flow through the second flow valve assembly 118b.

In an embodiment, a dynamic x-ray shielding garment 104 includes one or more x-ray radiation sensor devices 170 disposed on an x-ray source-side of the first layer 202 that acquire at least a portion of an incident x-ray radiation stimulus and transduce the incident x-ray radiation stimulus acquired by the x-ray radiation sensor device 170 into at least one measurand indicative of an incident x-ray flux during an integration period of the one or more x-ray radiation sensor devices 170. In an embodiment, a dynamic x-ray shielding garment 104 includes one or more x-ray radiation sensor devices 170 disposed on an x-ray source-side of the first layer 202 that detect an incident x-ray stimulus, and one or more x-ray radiation sensor devices 170 disposed on user-side of the first layer 202 that detect a transmitted x-ray stimulus. In an embodiment, a dynamic x-ray shielding garment 104 includes at least one computing device 122 that generates one or more parameters associated with a comparison between an incident x-ray stimulus and a transmitted x-ray stimulus.

In an embodiment, the dynamic x-ray shielding garment 104 includes one or more sensors 171 to determine a presence of the x-ray shielding fluid composition within one or more sites within the circulation network. In an embodiment, the dynamic x-ray shielding garment 104 includes one or more sensors 171 to determine a presence of the x-ray shielding fluid composition within one or more locations within the dynamic x-ray shielding garment. In an embodiment, the dynamic x-ray shielding garment 104 includes one or more sensors 171 to determine a presence of the x-ray shielding fluid composition within one or more of the plurality of interconnected interstitial spaces 110.

In an embodiment, a dynamic x-ray shielding garment 104 includes an x-ray shielding fluid supply controller 120 includes control logic 149 arranged to determine an actuate flow condition and to actuate the flow of the x-ray shielding fluid composition to or from the x-ray shielding fluid reservoir assembly 112, and along one or more of the plurality of interconnected interstitial spaces 110, responsive to the actuate flow condition. In an embodiment, the x-ray shielding fluid supply controller 120 actuates the flow of the x-ray shielding fluid composition to or from the x-ray shielding fluid reservoir assembly 112, and along one or more of the plurality of interconnected interstitial spaces 110, responsive to at least one of an authorization protocol, an authentication protocol, or an activation protocol. In an embodiment, the x-ray shielding fluid supply controller 120 includes a speech recognition module 123 that causes the x-ray shielding fluid supply controller 120 to modulate the flow of the x-ray shielding fluid composition to or from the x-ray shielding fluid reservoir assembly 112, and along one or more of the plurality of interconnected interstitial spaces 110, responsive to one or more audio inputs. In an embodiment, during operation, the x-ray shielding fluid supply controller 120 receives an input from the speech recognition module 123 associated with a verbal command to actuate flow to the x-ray shielding fluid composition. Responsive to the input from the speech recognition module 123, the x-ray shielding fluid supply controller 120 actuates at least one pump assembly 116 or flow valve assembly 118 to initiate the supply of x-ray shielding fluid composition to or from the x-ray shielding fluid reservoir assembly 112, and along a circulation network within the dynamic x-ray shielding device 102.

In an embodiment, the dynamic x-ray shielding garment 104 includes a power source 150 including at least one battery. In an embodiment, the dynamic x-ray shielding garment 104 includes a power source 150 wired, or wireless coupled, to an external source. In an embodiment, the dynamic x-ray shielding garment 104 includes a power source 150 including at least one of a thermoelectric generator, a piezoelectric generator, a microelectromechanical system generator, or a biomechanical-energy harvesting generator. In an embodiment, the dynamic x-ray shielding garment 104 includes a power source 150 electromagnetically, magnetically, ultrasonically, optically, inductively, electrically, or capacitively coupled to the x-ray shielding fluid supply controller 120. In an embodiment, the dynamic x-ray shielding garment 104 includes an energy transfer system 160 electromagnetically, magnetically, ultrasonically, optically, inductively, electrically, or capacitively coupled to the x-ray shielding fluid supply controller 120.

In an embodiment, the dynamic x-ray shielding garment 104 includes a pump assembly 116 including one or more pumps 117 that circulate the x-ray shielding fluid composition within at least a portion of the circulation network (mechanical, magnetic, etc.) For example, in an embodiment, the dynamic x-ray shielding garment 104 includes an x-ray shielding fluid composition pump assembly 116 that is in fluid communication with at least one of the x-ray shielding fluid reservoir assembly 112 or the circulation network that supplies and circulates the x-ray shielding fluid composition to or from the x-ray shielding agent reservoir assembly 112, and along one or more regions within the circulation network. In an embodiment, the dynamic x-ray shielding garment 104 includes one or more pumps 117 that employ magnetic forces on magnetic components of the x-ray shielding fluid composition to circulate the x-ray shielding fluid composition to or from the x-ray shielding agent reservoir assembly 112, and along one or more regions within the circulation network.

In an embodiment, the dynamic x-ray shielding garment 104 includes one or more valves 119 to selectively direct flow of the x-ray shielding fluid composition to or from the x-ray shielding agent reservoir 114. In an embodiment, the dynamic x-ray shielding garment 104 includes one or more valves 119 to selectively direct flow of the x-ray shielding fluid composition within the circulation network. In an embodiment, the dynamic x-ray shielding garment 104 includes at least a second x-ray shielding fluid reservoir assembly 112 including one or more x-ray shielding fluid reservoirs 114.

In an embodiment, the dynamic x-ray shielding garment 104 includes an x-ray shielding status reporter device 180 including one or more receivers 182, transceivers 184, or transmitters 186 that generate an output indicative of at least one of an x-ray shielding fluid composition presence within one or more regions of the plurality of interconnected interstitial spaces. In an embodiment, the dynamic x-ray shielding garment 104 includes an x-ray shielding status reporter device 180 including one or more receivers 182, transceivers 184, or transmitters 186 that generate an output indicative of x-ray sensor value. In an embodiment, the dynamic x-ray shielding garment 104 includes an x-ray shielding status reporter device 180 including one or more receivers 182, transceivers 184, or transmitters 186 that generate an output indicative of an authorization to x-ray source to irradiate. In an embodiment, the dynamic x-ray shielding garment 104 includes an x-ray shielding status reporter device 180 including one or more receivers 182, transceivers 184, or transmitters 186 that generate an output indicative of authorization to x-ray source spectrum or intensity.

In an embodiment, the dynamic x-ray shielding garment 104 includes an x-ray shielding status reporter device 180 including an irradiation authorization component 188 that generates one or more cryptographic keys that provide authorization to the external x-ray radiation-emitting system 146 to initiate x-ray radiation delivery. In an embodiment, the dynamic x-ray shielding garment 104 includes an x-ray shielding status reporter device 180 including an irradiation authorization component 188 that generates one or more cryptographic keys that provide authorization to the external x-ray radiation-emitting system 146 to initiate a spectrum-specific x-ray dose regimen. In an embodiment, the dynamic x-ray shielding garment 104 includes an x-ray shielding status reporter device 180 including an irradiation authorization component 188 that generates one or more cryptographic keys that provide authorization to the external x-ray radiation-emitting system 146 to initiate an intensity-specific x-ray dose regimen.

In an embodiment, the dynamic x-ray shielding garment 104 includes fluid supply controller 120 having one or more computing devices 122, operably coupled to one or more pump assemblies 116 including one or more pumps 117, that manage fluid flow of an x-ray shielding fluid composition to or from the x-ray shielding agent reservoir assembly 112, and along one or more of the plurality of interconnected interstitial spaces. In an embodiment, the dynamic x-ray shielding garment 104 includes an x-ray shielding status reporter device 180 that receives x-ray potential exposure event data associated with delivery of an x-ray radiation stimulus from an x-ray radiation-emitting system 146. In an embodiment, the x-ray shielding status reporter device 180 is operably coupled to one or more x-ray shielding fluid supply controllers 120 that direct fluid flow of an x-ray shielding fluid composition received in an x-ray shielding fluid reservoir assembly associated with a dynamic x-ray shielding garment, to or from the x-ray shielding agent reservoir, and along one or more of a plurality of interconnected interstitial spaces within the dynamic x-ray shielding garment 104, responsive to an output signal from the x-ray shielding status reporter device 180.

In an embodiment, the dynamic x-ray shielding garment 104 includes fluid supply controller 120 is configured to manage fluid flow of a gravity-fed x-ray shielding fluid composition to or from the x-ray shielding agent reservoir assembly 112, and along one or more of the plurality of interconnected interstitial spaces. In an embodiment, the dynamic x-ray shielding garment 104 includes fluid supply controller 120 is configured to manage fluid flow of a pressure-fed x-ray shielding fluid composition to or from the x-ray shielding agent reservoir assembly 112, and along one or more of the plurality of interconnected interstitial spaces.

FIG. 5 shows a dynamic x-ray shielding method 500. At 510, the dynamic x-ray shielding method 500 includes receiving x-ray potential exposure event data associated with delivery of an x-ray radiation stimulus from an x-ray radiation-emitting system 146. For example, in an embodiment, the dynamic x-ray shielding garment 104 includes an x-ray shielding status reporter device 180 having one or more receivers 182, transceivers 184, or transmitters 186 that receiving x-ray potential exposure event data associated with delivery of an x-ray radiation stimulus from an x-ray radiation-emitting system 146.

At 512, receiving the potential x-ray exposure event data includes initiating a data transmission transfer between a dynamic x-ray shielding device and an x-ray radiation-emitting system 146. At 514, receiving the potential x-ray exposure event data includes initiating a data transmission transfer between a dynamic x-ray shielding device and an x-ray radiation-emitting system 146 based on the identification of the x-ray radiation sensing device 170. At 516, receiving the potential x-ray exposure event data includes telemetrically receiving, via one or more receivers 182, transceivers 184, or transmitters 186, proposed dose data, time to exposure data, time to exposure data, or duration of exposure data. At 518, receiving the potential x-ray exposure event data includes wirelessly receiving at least one of radiation intensity data, radiation energy data, radiation exposure time data, rate of radiation energy deposition, depth of radiation energy deposition data, absorbed dose data, absorbed dose rate data, committed effective dose data, cumulative dose data, effective dose data, equivalent dose data, or exposure data associated with the potential x-ray exposure event.

At 520, the dynamic x-ray shielding method 500 includes directing fluid flow of an x-ray shielding fluid composition received in an x-ray shielding fluid reservoir assembly 112 associated with a dynamic x-ray shielding garment, to or from the x-ray shielding agent reservoir, and along one or more of a plurality of interconnected interstitial spaces 110 within the dynamic x-ray shielding garment, responsive to the x-ray potential exposure event data.

For example, in an embodiment, the dynamic x-ray shielding garment includes 104 an x-ray shielding fluid supply controller 120 that is operable to directing fluid flow of an x-ray shielding fluid composition received in the x-ray shielding fluid reservoir assembly 116 associated with the dynamic x-ray shielding garment 104, to or from the one or more x-ray shielding agent reservoirs 117, and along one or more of a plurality of interconnected interstitial spaces 110 within the dynamic x-ray shielding garment, responsive to the x-ray potential exposure event data.

At 522, directing the fluid flow of the x-ray shielding fluid composition includes directing a flow sufficient of the x-ray shielding fluid composition to modulate at least one of a penetration depth, intensity, or energy associated with the x-ray radiation stimulus. At 524, directing the fluid flow of the x-ray shielding fluid composition includes directing a flow sufficient of the x-ray shielding fluid composition to cause at least a portion of the dynamic x-ray shielding garment to have an x-ray shielding lead equivalence of about 0.25 millimeters to about 0.5 millimeters. At 526, directing the fluid flow of the x-ray shielding fluid composition includes directing a flow sufficient of the x-ray shielding fluid composition to cause at least a portion of the dynamic x-ray shielding garment to have an x-ray shielding lead equivalence of greater than about 0.25 millimeters.

FIG. 6 shows an x-ray shielding method 600. At 610, the x-ray shielding method 600 includes actuating fluid flow of an x-ray shielding fluid composition received in one or more x-ray shielding fluid reservoirs associated with a dynamic x-ray shielding garment, to or from the x-ray shielding agent reservoir, and along one or more of a plurality of interconnected interstitial spaces 110 within the dynamic x-ray shielding garment responsive to a determination that an x-ray radiation-emitting system 146 is in operation. At 620, the x-ray shielding method 600 includes actuating fluid flow of an x-ray shielding fluid composition received in one or more x-ray shielding fluid reservoirs associated with a dynamic x-ray shielding garment, to or from the x-ray shielding agent reservoir, and along one or more of a plurality of interconnected interstitial spaces 110 within the dynamic x-ray shielding garment responsive to an input associated with a potential delivery of an x-ray radiation stimulus from an x-ray radiation-emitting system 146. At 630, the x-ray shielding method 600 includes receiving x-ray potential exposure event data associated with delivery of an x-ray radiation stimulus from an x-ray radiation-emitting system 146. At 640, the x-ray shielding method 600 includes concurrent or sequential actuating fluid flow of a first x-ray shielding fluid composition or the second x-ray shielding fluid, received in an x-ray shielding fluid reservoir assembly 112, to or from the x-ray shielding agent reservoir and along respectively one of a first flow path 204 or a second flow path 210 of a dynamic x-ray shielding apparatus, responsive to potential exposure event data indicative of an x-ray potential exposure event.

FIG. 7 shows a dynamic x-ray shielding method 700. At 710, the dynamic x-ray shielding method 700 includes determining an actuate flow condition. At 720, the dynamic x-ray shielding method 700 includes concurrent or sequential actuating fluid flow of a first x-ray shielding fluid composition or the second x-ray shielding fluid, received in a plurality of x-ray shielding fluid reservoirs, to or from the plurality of x-ray shielding fluid reservoirs and along respectively one of a first flow path 204 or a second flow path 210 of a dynamic x-ray shielding apparatus, responsive to the actuate flow condition.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for detecting position and/or velocity, control motors for moving and/or adjusting components and/or quantities). A data processing system can be implemented utilizing suitable commercially available components, such as those typically found in data computing/communication and/or network computing/communication systems.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware in one or more machines or articles of manufacture), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation that is implemented in one or more machines or articles of manufacture; or, yet again alternatively, the implementer may opt for some combination of hardware, software, and/or firmware in one or more machines or articles of manufacture. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware in one or more machines or articles of manufacture.

The herein described subject matter sometimes illustrates different components contained within, or connected with, different other components. It is to be understood that such depicted architectures are merely examples, and that in fact, many other architectures can be implemented that achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably coupleable," to each other to achieve the desired functionality. Specific examples of operably coupleable include, but are not limited to, physically mateable and/or physically interacting components, and/or wirelessly interactable, and/or wirelessly interacting components, and/or logically interacting, and/or logically interactable components.

In an embodiment, one or more components may be referred to herein as "configured to," "configurable to," "operable/operative to," "adapted/adaptable," "able to," "conformable/conformed to," etc. Such terms (e.g., "configured to") can generally encompass active-state components and/or inactive-state components and/or standby-state components, unless context requires otherwise.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by the reader that each function and/or operation within such block diagrams, flowcharts, or examples can be implemented, individually and/or collectively, by a wide range of hardware, software, firmware in one or more machines or articles of manufacture, or virtually any combination thereof. Further, the use of "Start," "End," or "Stop" blocks in the block diagrams is not intended to indicate a limitation on the beginning or end of any functions in the diagram. Such flowcharts or diagrams may be incorporated into other flowcharts or diagrams where additional functions are performed before or after the functions shown in the diagrams of this application. In an embodiment, several portions of the subject matter described herein is implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal-bearing medium used to actually carry out the distribution. Non-limiting examples of a signal-bearing medium include the following: a recordable type medium such as a floppy disk, a hard disk drive, a Compact Disc (CD), a Digital Video Disk (DVD), a digital tape, a computer memory, etc., and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

While particular aspects of the present subject matter described herein have been shown and described, it will be apparent to the reader that, based upon the teachings herein, changes and modifications can be made without departing from the subject matter described herein and its broader aspects and, therefore, the appended claims are to encompass within their scope all such changes and modifications as are within the true spirit and scope of the subject matter described herein. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). Further, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, the operations recited therein generally may be performed in any order. Also, although various operational flows are presented in a sequence(s), it should be understood that the various operations may be performed in orders other than those that are illustrated, or may be performed concurrently. Examples of such alternate orderings includes overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. An x-ray shielding fluid composition, comprising:
   a carrier fluid;
   a first plurality of x-ray shielding particles disposed in the carrier fluid, each of the x-ray shielding particles having at least a first x-ray shielding agent and a second x-ray shielding agent, the second x-ray shielding agent having one or more absorption edges different from the first x-ray shielding agent; and
   wherein the plurality of x-ray shielding particles includes glass beads each having a plurality of x-ray shielding agents within a glass material matrix.

2. The x-ray shielding fluid composition of claim 1, the first plurality of x-ray shielding particles further comprising a third x-ray shielding agent having one or more absorption edges different from the second x-ray shielding agent and the first x-ray shielding agent.

3. The x-ray shielding fluid composition of claim 2, the first plurality of x-ray shielding particles further comprising a fourth x-ray shielding agent having one or more absorption edges different from the third x-ray shielding agent, the second x-ray shielding agent, and the first x-ray shielding agent.

4. The x-ray shielding fluid composition of claim 3, the first plurality of x-ray shielding particles further comprising a fifth x-ray shielding agent having one or more absorption edges different from the fourth x-ray shielding agent, the third x-ray shielding agent, the second x-ray shielding agent, and the first x-ray shielding agent.

5. The x-ray shielding fluid composition of claim 1, wherein the second x-ray shielding agent includes an x-ray mass attenuation coefficient different from the first x-ray shielding agent.

6. The x-ray shielding fluid composition of claim 1, wherein the second x-ray shielding agent includes at least one k-edge having an energy level lower than at least one k-edge of the first x-ray shielding agent.

7. The x-ray shielding fluid composition of claim 1, wherein the second x-ray shielding agent includes at least one k-edge or l-edge corresponding to an x-ray energy absorption minimum of the first x-ray shielding agent.

8. The x-ray shielding fluid composition of claim 1, wherein each of the first plurality of x-ray shielding particles includes a plurality of elemental dopants within the glass material matrix.

9. The x-ray shielding fluid composition of claim 1, wherein each of the first plurality of x-ray shielding particles includes a plurality of elemental dopants within the glass material matrix, the plurality of dopants forming the second x-ray shielding agent.

10. The x-ray shielding fluid composition of claim 1, further comprising a second plurality of x-ray shielding particles disposed in the carrier fluid, each of the second plurality of x-ray shielding particles including at least a third x-ray shielding agent having one or more absorption edges different from the second x-ray shielding agent and the first x-ray shielding agent.

11. The x-ray shielding fluid composition of claim 1, wherein at least one of the first x-ray shielding agent and the second x-ray shielding agent includes at least one material that absorbs x-rays at one or more frequencies and fluoresce x-rays at one or more lower frequencies.

12. The x-ray shielding fluid composition of claim 1, wherein at least one of the first x-ray shielding agent and the second x-ray shielding agent includes one or more $SiO_2$—PbO-alkali metal oxide glasses, CaO—SrO—$B_2O_3$ glasses, or boron-lithium glasses.

13. The x-ray shielding fluid composition of claim 1, wherein at least one of the first x-ray shielding agent and the second x-ray shielding agent includes borated high density polyethylene.

14. The x-ray shielding fluid composition of claim 1, wherein at least one of the first x-ray shielding agent and the second x-ray shielding agent includes at least one of $C_{10}H_8O_4$, $C_8H_7Cl$, $C_8H_8$, poly(methyl methacrylate) (PMMA), polycarbonate ($C_{16}H_{14}O_3$), polyethylene, or ultra-high molecular-weight polyethylene.

15. The x-ray shielding fluid composition of claim 1, wherein at least one of the first x-ray shielding agent and the second x-ray shielding agent includes silicon nitride ($Si_3N_4$).

16. The x-ray shielding fluid composition of claim 1, wherein the carrier fluid includes a fluid material having one or more x-ray absorption edges.

17. The x-ray shielding fluid composition of claim 1, wherein the carrier fluid includes a fluid material having one or more x-ray absorption edges different from the second x-ray shielding agent and the first x-ray shielding agent.

18. The x-ray shielding fluid composition of claim 1, further comprising one or more anti-flocculant agents.

19. The x-ray shielding fluid composition of claim 1, wherein at least some of the first plurality of x-ray shielding particles are coated with an anti-flocculant coating.

20. The x-ray shielding fluid composition of claim 1, wherein at least one of the first x-ray shielding agent and the second x-ray shielding agent includes at least one of lead (Pb), lithium fluoride (LiF), tantalum (Ta), or tungsten (W).

21. The x-ray shielding fluid composition of claim 1, wherein at least one of the first x-ray shielding agent and the second x-ray shielding agent includes $C_2F_4$.

22. The x-ray shielding fluid composition of claim 1, wherein the carrier fluid includes a gas carrier.

23. The x-ray shielding fluid composition of claim 1, wherein the carrier fluid includes an aerosol.

24. The x-ray shielding fluid composition of claim 1, wherein the carrier fluid includes two or more immiscible liquids.

* * * * *